US009610048B2

(12) United States Patent
Vij et al.

(10) Patent No.: US 9,610,048 B2
(45) Date of Patent: Apr. 4, 2017

(54) FIBER OPTIC SYSTEMS FOR MRI SUITES AND RELATED DEVICES AND METHODS

(71) Applicant: MRI Interventions, Inc., Memphis, TN (US)

(72) Inventors: Kamal Vij, Chandler, AZ (US); Peter Piferi, Orange, CA (US); Richard James Kail, Santa Ana, CA (US)

(73) Assignee: MRI Interventions, Inc., Irvine, CA (US)

( * ) Notice: Subject to any disclaimer, the term of this patent is extended or adjusted under 35 U.S.C. 154(b) by 1080 days.

(21) Appl. No.: 13/772,822

(22) Filed: Feb. 21, 2013

(65) Prior Publication Data

US 2014/0046167 A1 Feb. 13, 2014

Related U.S. Application Data

(60) Provisional application No. 61/681,216, filed on Aug. 9, 2012.

(51) Int. Cl.
*G06F 3/033* (2013.01)
*G09G 5/08* (2006.01)
*A61B 5/00* (2006.01)
*A61B 5/055* (2006.01)

(52) U.S. Cl.
CPC .......... *A61B 5/7475* (2013.01); *A61B 5/0046* (2013.01); *A61B 5/055* (2013.01)

(58) Field of Classification Search
CPC . A61B 18/1492; A61B 19/50; A61B 19/5244; A61B 19/56; A61B 2017/00053; A61B 2017/00243; A61B 2018/00029; A61B 2018/00839; A61B 2018/1472; A61B 2019/501; A61B 2019/505; A61B 2019/507; A61B 2019/5236; A61B 2019/05; A61B 5/0046; A61B 5/055
See application file for complete search history.

(56) References Cited

U.S. PATENT DOCUMENTS

| 6,050,992 A | 4/2000 | Nichols |
| 6,167,311 A | 12/2000 | Rezai |
| 6,184,521 B1 * | 2/2001 | Coffin, IV .......... A61B 5/14552 250/216 |

(Continued)

OTHER PUBLICATIONS

Data Sheet for Optical USB Extension Cable, Opticis, Jan. 21, 2008, 5 pages.

*Primary Examiner* — Amare Mengistu
*Assistant Examiner* — Crystal A Mathews
(74) *Attorney, Agent, or Firm* — Myers Bigel, P.A.

(57) ABSTRACT

Fiber optic systems with an MR compatible mouse in an MR scanner room that connects to a fiber optic computer mouse interface that is attached to a fiber optic cable that connects to a USB port of a computer in the MR control room to allow the mouse in the MR scanner room to move a cursor on a monitor in communication with the computer in the control room of an MRI suite during an MRI guided surgical procedure. The fiber optic cable(s) can be routed though a conventional RF wall waveguide and avoids the need for additional holes in the penetration panel for connectors. The fiber optic systems can also include up converters and down converters for providing fiber optic video signals from cameras in the MR scanner room to display video signal on the monitor.

22 Claims, 13 Drawing Sheets

(56) References Cited

U.S. PATENT DOCUMENTS

| | | | |
|---|---|---|---|
| 6,198,285 B1 | 3/2001 | Kormos et al. | |
| 6,356,786 B1 | 3/2002 | Rezai et al. | |
| 6,400,155 B2 | 6/2002 | Kormos et al. | |
| 6,405,079 B1 | 6/2002 | Ansarinia | |
| 6,438,423 B1 | 8/2002 | Rezai et al. | |
| 6,483,719 B1* | 11/2002 | Bachman | H05K 9/003 174/378 |
| 6,526,318 B1 | 2/2003 | Ansarinia | |
| 6,539,263 B1 | 3/2003 | Schiff et al. | |
| 6,600,479 B1* | 7/2003 | Smith | G06F 3/03543 345/156 |
| 6,609,030 B1 | 8/2003 | Rezai et al. | |
| 6,708,064 B2 | 3/2004 | Rezai | |
| 7,039,266 B1* | 5/2006 | Doty | G01R 33/283 385/13 |
| 7,189,103 B1* | 3/2007 | Brown | H01R 43/0263 439/493 |
| 7,283,860 B2* | 10/2007 | Frazier | G01R 33/283 600/407 |
| 7,501,824 B2* | 3/2009 | Kawachi | G01R 33/28 324/318 |
| 8,208,993 B2 | 6/2012 | Piferi et al. | |
| 8,214,012 B2 | 7/2012 | Zuccolotto et al. | |
| 8,509,876 B2* | 8/2013 | Karmarkar | A61N 1/0529 324/318 |
| 2002/0063688 A1* | 5/2002 | Shaw | G06F 3/0312 345/163 |
| 2002/0063935 A1* | 5/2002 | Price | H04B 10/505 398/182 |
| 2004/0030233 A1* | 2/2004 | Frazier | G01R 33/283 600/410 |
| 2005/0273000 A1* | 12/2005 | Dinehart | G01R 33/283 600/410 |
| 2006/0094286 A1* | 5/2006 | Lee | G06F 1/266 439/489 |
| 2007/0002020 A1* | 1/2007 | Ranta | G06F 3/0317 345/166 |
| 2007/0152966 A1* | 7/2007 | Krah | G06F 3/016 345/163 |
| 2008/0122791 A1* | 5/2008 | Hsu | G06F 3/03543 345/165 |
| 2009/0093705 A1* | 4/2009 | Vangdal | G01R 33/283 600/410 |
| 2009/0171184 A1 | 7/2009 | Jenkins et al. | |
| 2009/0189988 A1* | 7/2009 | Jia | G05B 19/042 348/211.4 |
| 2009/0195514 A1* | 8/2009 | Glynn | A61B 8/12 345/173 |
| 2009/0196621 A1* | 8/2009 | Chen | G06F 13/4027 398/115 |
| 2009/0234218 A1* | 9/2009 | Washburn | A61B 5/055 600/410 |
| 2010/0150572 A1* | 6/2010 | Lee | G06F 13/409 398/141 |
| 2010/0312096 A1 | 12/2010 | Guttman | |
| 2011/0208980 A1* | 8/2011 | Brooks | G06F 1/266 713/300 |
| 2011/0234497 A1* | 9/2011 | Zahnert | H04N 1/107 345/166 |
| 2012/0013525 A1* | 1/2012 | Trcka | G01R 33/283 345/8 |
| 2012/0319975 A1* | 12/2012 | Fuchs | G06F 3/0416 345/173 |
| 2013/0162510 A1* | 6/2013 | Ohgishi | G01R 33/283 345/107 |
| 2013/0182085 A1* | 7/2013 | Ziarati | A61B 5/055 348/51 |
| 2013/0333477 A1* | 12/2013 | Kataoka | G01H 9/00 73/655 |
| 2014/0244880 A1* | 8/2014 | Soffer | G06F 3/0227 710/300 |
| 2016/0051187 A1* | 2/2016 | Damadian | A61B 5/4848 600/411 |

\* cited by examiner

FIG. 6C  LASER LIGHT WINDOW

FIBER OPTIC SYSTEMS FOR MRI SUITES AND RELATED DEVICES AND METHODS

RELATED APPLICATIONS

This application claims the benefit of and priority to U.S. Provisional Patent Application Ser. No. 61/681,216 filed Aug. 9, 2012, the contents of which are hereby incorporated by reference as if recited in full herein.

FIELD OF THE INVENTION

The present invention relates generally to communication interfaces that connect control user interfaces (UI) in an MRI Scanner room to devices in a control room with an RF shielded wall therebetween.

BACKGROUND OF THE INVENTION

MRI suites have a control room with MRI Scanner operating components such as an RF amplifier and control cabinet (typically called the control room) and a separate room or chamber holding a high field magnet in which a patient is placed for an MRI procedure (typically called the Scanner room). MRI suites are enclosed in a Faraday shield (e.g., RF shielding) in order to electrically isolate sensitive MRI radio receivers and prevent them from picking up RF signals other than those emitted by the patient under examination. An RF-shielded wall separates the two rooms. A removable portion of the RF-shielded wall is typically called the penetration panel. RF shielding is important because it isolates the MRI scanner from external RF sources that can cause artifacts in the MRI image. For a typical MRI scanner chamber, the RF shielding causes at least 100 dB of signal attenuation of signals in the frequency range of 1 Hz to 150 MHz. Holes or openings made in this shielding can compromise the shielding effectiveness.

In most MRI suites, a grounded tubular waveguide provides the only access space for non-metallic cables, tubes, water or gas lines, and the like between the control room and the Scanner room. All other electrical cables have feedthrough filters that are built on the penetration panel which is electrically connected to the Faraday shield. The waveguide is a circular pipe made of copper or brass that extends out a distance on each side of the penetration panel.

Waveguide depth and diameter is based on the fact that an electromagnetic field attenuates rapidly down a small diameter hole of sufficient depth, providing certain conditions are met. Thus, the diameter and length of the waveguide are chosen to inhibit or prevent RF waves from passing through it. Using the waveguide in this manner is commonly called "waveguide below cutoff". This guideline allows small diameter holes to be made in conductive enclosures, as may be needed for ventilation, or as a pass-through for non-metallic members. Shielding effectiveness of an MRI suite can be compromised by inserting metallic components like cable through the waveguide or by using unfiltered or improperly filtered electrical connections.

MRI-guided interventional surgeries can require many types of electrical leads to operate properly. For example, as described in U.S. patent application Ser. No. 12/236,854, entitled MRI Surgical Systems For Real-Time Visualizations Using MRI Image Data And Predefined Data Of Surgical Tools (which describes components of, inter alia, a neurosurgery system also known as the CLEARPOINT® interventional system from MRI Interventions, Inc., Memphis, Tenn.) surgical systems can have connections or leads for MRI compatible cameras, data cable, mouse or trackball lead, monitor leads, video display monitors and/or other electrical inputs that require RF filters. U.S. patent application Ser. No. 12/237,033 describes MRI interventional systems with video cameras. See also, U.S. patent application Ser. No. 12/796,017, filed Jun. 8, 2012, entitled MRI-Guided Interventional Systems That Can Track And Generate Dynamic Visualizations Of Flexible Intrabody Devices In Near Real Time (which also describes components of, inter alia, a cardiac system also known as the CLEARTRACE® interventional system from MM Interventions, Inc., Memphis, Tenn.). In the past, relatively large "custom" openings were cut into penetration panels to support the required cabling for the intervention system. Removable filter boxes have also been used to help avoid permanent modification to MRI suites, see, e.g., co-assigned PCT/US2012/037334. The contents of the patent applications cited above are hereby incorporated by reference as if recited in their entirety herein.

SUMMARY OF EMBODIMENTS OF THE INVENTION

Embodiments of the invention provide a computer interface mouse with fiber optic interfaces that use fiber optic cables that extend through the wave guide (or through connectors in the penetration panel) and connect devices on the scanner room side to devices on the control room side.

The systems can be configured to allow for easy installation without requiring any physical modification to the RF shielding or penetration panel.

Some embodiments are directed to surgical systems for an MRI suite. The systems include an MRI compatible mouse residing in an MR Scanner room of the MRI suite, a fiber optic mouse interface in the MR Scanner room in communication with the mouse, and a fiber optic cable attached to the fiber optic mouse interface configured to connect a computer outside the MR scanner room. A user is able to move the mouse in the MR Scanner room to move a cursor on the monitor and/or select actions or functions in drop down menus presented by the computer to a monitor.

The system can include an up converter device in the MR scanner room in communication with a down converter device outside the MR scanner room. The video to fiber optic signal can be converted and transmitted by the up converter to the down converter which converts fiber optic signal to video and transmits the video to the monitor.

The fiber optic cable can be routed through a waveguide in an RF shielded wall that extends between the MR scanner room and an MR control room of the MRI suite.

The system can include a length of RF shielded cable attached to the mouse and extending between the mouse and the fiber optic mouse interface.

The up converter device can include a DC power supply that is configured to power the fiber optic mouse interface.

The up converter device can include a perimeter with at least a portion having a ground shield to suppress EMI.

The fiber optic mouse interface can include a USB to optical converter and non-ferromagnetic housing with EMI grounding, power input and USB mouse connectors.

The fiber optic mouse interface can include a housing with a perimeter having a ground shield on walls thereof.

The mouse can have a single tactile switch allowing for left click input.

The mouse can have non-ferromagnetic screws holding a primary circuit board in a mouse housing. The mouse can include an EMI ground shield under the primary circuit board.

The system can include a second circuit board holding DC power supply filter wires and serial data lines that connect to the primary circuit board.

The system can include a video to fiber optic up converter device in the MR scanner room. The up converter device can include at least one camera connector port, a mouse power port, a fiber optic output port and an AC voltage power input port. The mouse power port can be configured to engage a power cord that supplies DC voltage to the fiber optic mouse interface.

The system can include a fiber optic to video down converter device outside the MR scanner room (such as, for example, in the MR control room). The down converter device can be in communication with the computer and at least one monitor. The down converter device can include at least one optical input port configured to engage a fiber optic cable, at least one fiber optic video receiver, and at least one BNC video output.

The system can include a monitor in the MR scanner room that is connected to a VGA switch outside the MR scanner room via a fiberoptic monitor cable. The mouse is not attached to the monitor in the MR scanner room.

Other embodiments are directed to methods of controlling an MRI guided surgery. The methods include: (a) accepting user input from a mouse in an MR scanner room of an MRI suite; (b) converting signal from the mouse to a fiber optic mouse signal in the MR scanner room; (c) transmitting the fiber optic mouse signal to a USB port on a computer outside the MR scanner room via a fiberoptic cable that is routed through a waveguide in an RF shielded wall between the MR scanner room and an MR control room of the MRI suite; and (d) electronically moving a cursor on a monitor in outside the MR scanner room in communication with the computer using the transmitted fiber optic mouse signal.

The moving step can be carried out to control actions in a defined workflow associated with an MRI guided surgical procedure provided by the computer outside the scanner room to the outside the scanner room.

The method can include transmitting fiber optic signal from the computer in the control room to a monitor in the MR Scanner room. The mouse is not attached to the monitor in the MR Scanner room.

Other embodiments are directed to surgical systems for an MRI suite. The systems include: (a) an MRI compatible mouse residing in an MR Scanner room of the MRI suite; (b) a fiber optic mouse interface in the MR Scanner room in communication with the mouse; (c) a fiber optic cable attached to the fiber optic mouse interface connected to a computer in communication with at least one monitor outside the MR Scanner room so that a user is able to move the mouse in the MR Scanner room to (i) move a cursor and/or (ii) select functions or actions in drop down menus presented by the monitor outside the MR Scanner room; and (d) an up-converter device in the MR Scanner room in communication with a down-converter device outside the MR Scanner room, wherein video to fiber optic signal is converted and transmitted by the up-converter to the down-converter which converts fiber optic signal to video.

The system can also include a monitor in the MR Scanner room that is connected to a VGA switch outside the MR Scanner room via a fiberoptic monitor cable but the mouse is not attached to the monitor in the MR Scanner room (it controls a cursor/input on an external computer monitor or display and the external computer provides signal to the in-room monitor).

Still other embodiments are directed to MRI compatible fiber optic mouse suitable for operation in a an MRI Scanner room of a medical MRI suite holding a high field magnet. The mouse includes: (i) an MRI compatible mouse housing comprising non-ferromagnetic screws holding a primary circuit board therein; (ii) at least one external tactile switch allowing for left click input held by the mouse housing; and (iii) an EMI ground shield residing in the mouse housing under the primary circuit board.

The mouse housing can include a second circuit board holding DC power supply filter wires and serial data lines that connect to the primary circuit board.

The mouse can be sterile for use in a surgical environment.

The mouse can include first and second EMI suppressors, one with a ground input connected to the EMI ground shield and one with a ground input connected to a shield of a cable attached to the mouse and extending external thereof.

Still other embodiments are directed to surgical systems for an MRI suite. The systems include an up-converter device in the MR Scanner room in communication with a down-converter device outside the MR Scanner room. Video to fiber optic signal is converted and transmitted by the up-converter to the down-converter which converts fiber optic signal to video and transmits the video to a monitor outside the MR Scanner room.

The up-converter device can include at least one camera connector port, a mouse power port, a fiber optic output port and an AC voltage power input port.

The mouse power port can engage a power cord that supplies DC voltage to a fiber optic mouse interface that resides in the MR Scanner room. The system can include a fiber optic mouse attached to the fiber optic mouse interface and a monitor in the MR Scanner room. The fiber optic mouse can be detached from (not attached to) the monitor in the MR Scanner room.

The down-converter device can be in communication with a computer outside the MR Scanner room and at least one monitor. The down-converter device can include at least one optical input port configured to engage a fiber optic cable, at least one fiber optic video receiver, and at least one BNC video output.

The system can include a monitor in the MR Scanner room that is connected to a VGA switch outside the MR Scanner room via a fiberoptic monitor cable.

The up-converter device can include a housing having a perimeter with at least a portion having a ground shield to suppress EMI.

The system can include at least one camera in the MR Scanner room positioned to be in visual communication with a patient in a magnet and connected to the up-converter.

The system can include transmitter interface assembly with a housing shielding a transmitter that is in communication with the down converter and is configured to convert HDMI video signal from the down converter to fiber optic signal.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. The foregoing and other aspects of the present invention are explained in detail in the specification set forth below.

BRIEF DESCRIPTION OF THE DRAWINGS

FIG. 6C is a top view of the mouse with the circuit board removed to illustrate the shielding that resides under the mouse or primary PCB according to embodiments of the present invention.

DETAILED DESCRIPTION OF EMBODIMENTS OF THE INVENTION

Figure 1:
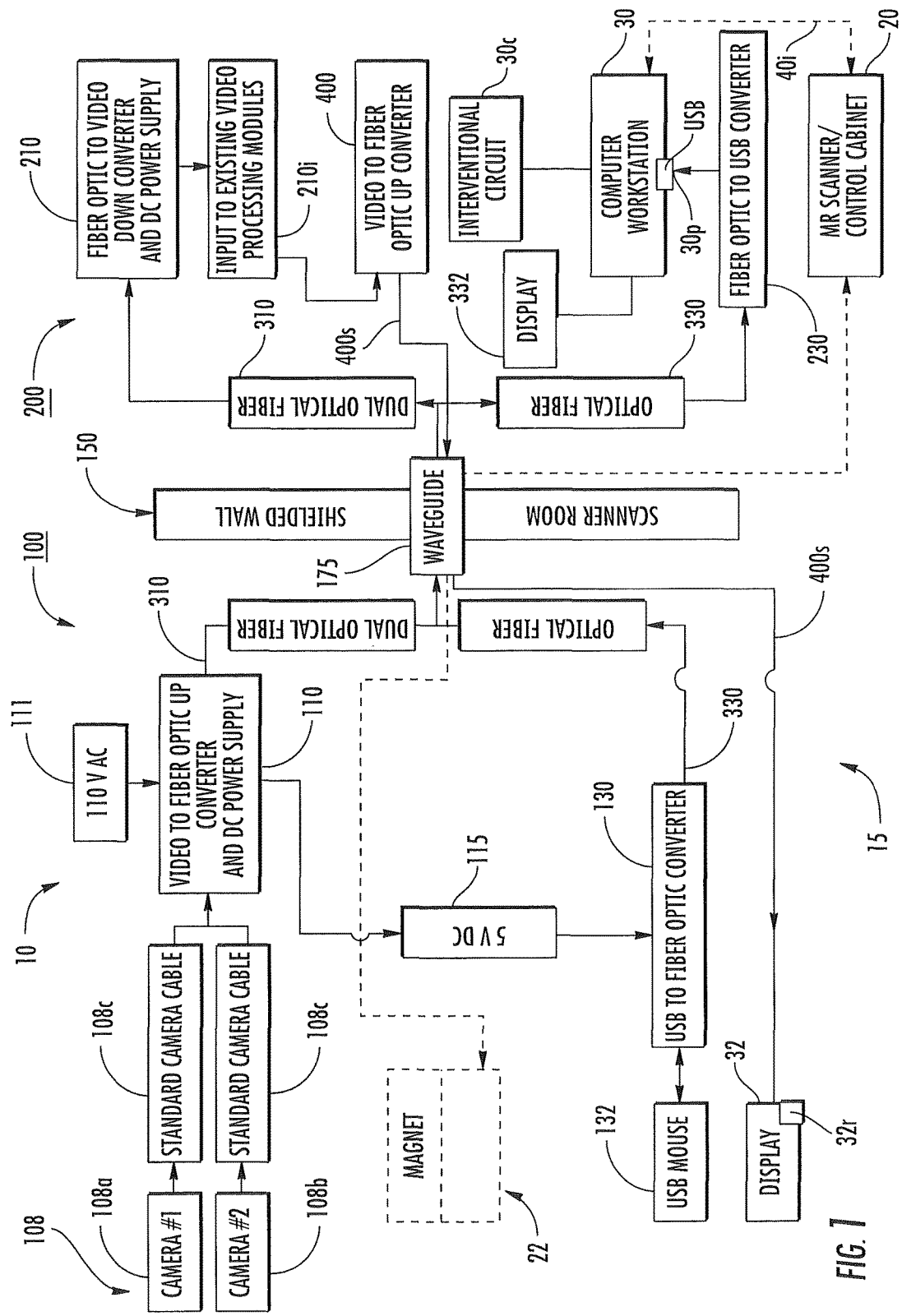
FIG. 1 is a schematic illustration of an MRI suite with control room components connected to Scanner room components using fiber optic cables routed through a waveguide in a RF shielded wall between the rooms according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "lead" means an electrical path created by one or more wires. The wires are typically insulated wires, particularly where exposed. The term "cable" can refer to an electrical cable or a fiber optic cable.

The term "about" means that the noted parameter can vary somewhat from the stated number, typically by +/−20%.

The term "MRI suite" refers to an enclosure that includes at least two rooms or chambers separated by RF shielding and/or an RF shielded wall as is well known to those of skill in the art.

The term "mouse" refers to a small device that a user moves across a surface in order to move a cursor to point to a place on a display screen or monitor and/or to select one or more actions. The term "computer" refers to a device with at least one digital signal processor and/or data processing system. The term "MRI-compatible" means that a device is safe for use in an MRI environment and/or that a device that can operate as intended in an MRI environment and not introduce artifacts into MRI signal data. As such, if residing within the high-field strength region of the magnetic field of an MRI suite, the MRI-compatible device is typically made of a non-ferromagnetic MRI-compatible material(s) suitable to reside and/or operate in a high magnetic field environment. The term "RF safe" means that the lead or probe is configured to safely operate when exposed to RF signals, particularly RF signals associated with MRI systems, without inducing unplanned current that inadvertently unduly heats local tissue or interferes with the planned therapy or procedure. The term "shield" and derivatives thereof refer to an RF shield that can attenuate unwanted RF signal. The new fiber optic system has been configured so that the 100 dB shielding in the MRI scanner room is not compromised. Shielding of items in the control room does not affect MRI images. These items can be shielded in order to pass the FCC emissions and IEC emissions requirements.

The term "high magnetic field" refers to magnetic fields above 0.5 T, typically between 1.5 T to 10 T, such as about 3.0 T and includes-high-field magnet closed bore and open bore MRI systems.

Turning now to the figures, FIG. 1 shows an exemplary MRI suite with a MRI Scanner room 100 (that holds a magnet 22, typically a high field magnet), and a control room 200 (that can hold a control cabinet 20 with RF amplifiers, gradient amplifiers or circuits associated therewith) with an exemplary layout of a fiber optic-based operating system 10 that connects certain components with fiber optic cable 330 (and 310, where video is used) on each side of the RF shielded wall 150.

As shown, in the MR scanner room 100, major components of this system 10 can include a mouse 132, a monitor or display 32, and a fiber-optic interface 130 for the mouse 132, which is typically configured to connect to a monitor or display 32 via a USB port. The fiber-optic mouse interface 130 is configured to provide a mouse connection from inside the MRI scanner room 100 to a computer outside the scanner room, such as the computer work station 30 located in the control room 200. The workstation 30 can have an interface 40i that connects to the MR scanner control cabinet 20. The fiber optic to USB converter 130 can be configured with a fiber optic cable 330 to connect/plug into the USB port 30p of the computer work station 30 and allows the mouse 132 that is located inside the MRI scanner room 100 to control the cursor location and software running on the monitor 332 of the computer work station 30 which is outside the scanner room 100, typically in the control room 200. However, the mouse 132 can communicate with the computer workstation 30 or CPU circuit 30c that can reside in other remote locations such as a remote site at a clinical site, in an equipment room or other location that allows for sufficiently fast interactive responses that facilitate an MRI-guided surgery. Thus, while embodiments of the system as described below show the workstation/computer 30 and/or circuit 30c in the control room 200, the computer 30 and/or circuit 30c may reside in other remote (outside of the scanner room) locations.

Figure 9:
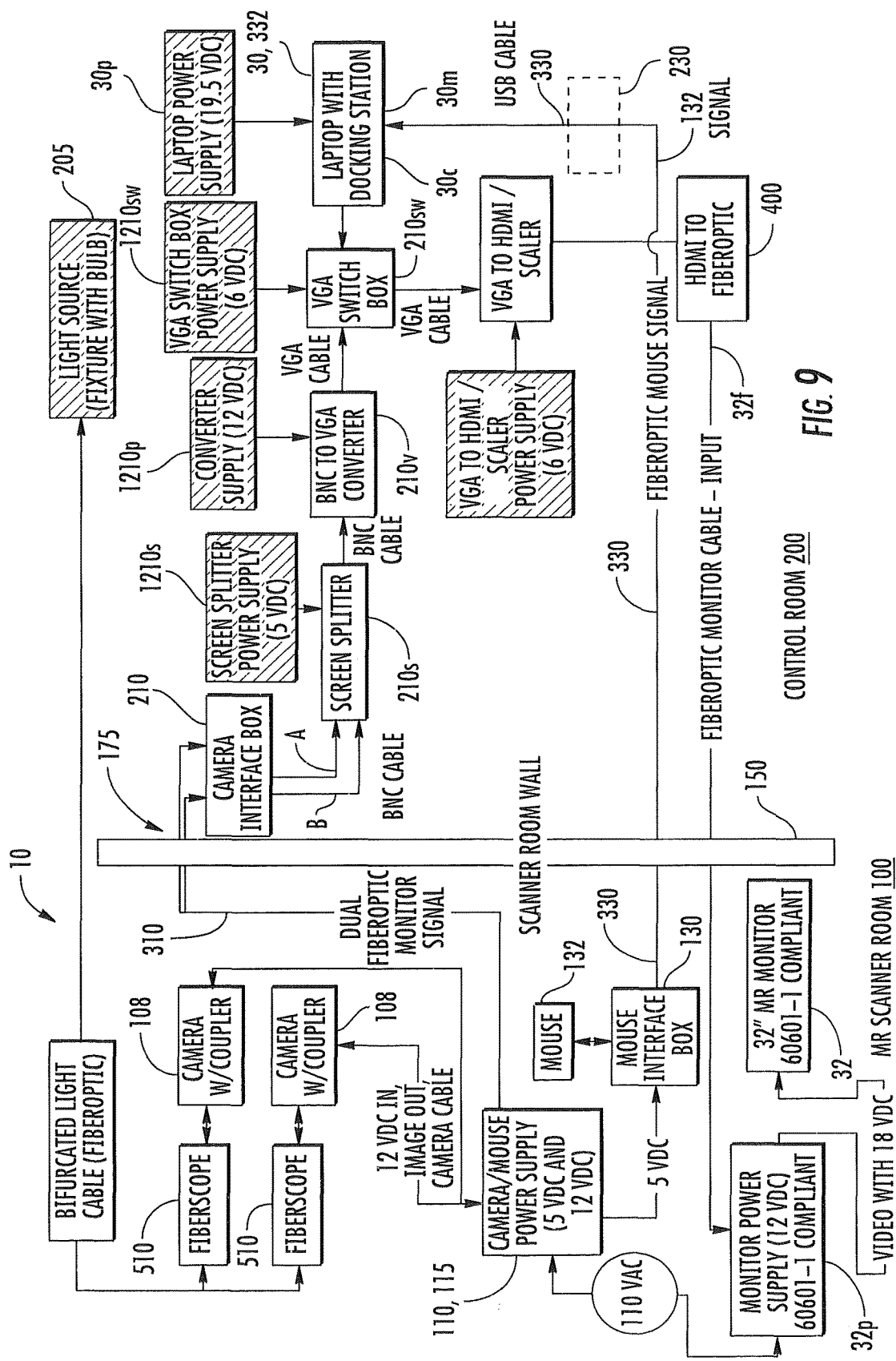
FIG. 9 is a schematic illustration of an MRI suite electrical circuit having a mouse and camera in the MR Scanner room with fiber optic cables that extend to the control room and associated interfaces according to embodiments of the present invention.

As shown in FIGS. 1, 9, 11A and 11B, for example, the system 10 can include a transmitter interface assembly 400 (which can also called a "Fiberoptic Interface Box" or "FIB") which is held in a housing 400h, such as a box or other suitable container. The housing 400h holds a transmitter/fiberoptic converter 404 that converts the video signal coming from the control room 200 into a fiberoptic signal 400s to go into the scanner room 100 and to display 32. As shown in FIGS. 1 and 9, the FIB 400 is in communication with the converter 210 and is connected to the scanner room display 32. The transmitter interface assembly 400 can be held in a separate device as shown or may be combined with other components and/or subassemblies in the control room 200.

The MR scanner control cabinet 20 includes a controller/processor (programmed with operational protocols and the like, and that controls pulse sequences and the like) that resides in the control room 200 while the magnet 22 resides in the Scanner room 100.

The MRI suite can include an MRI guided interventional system 10 with components that communicate with the MRI scanner control cabinet 20 in the control room 200. The system 10 includes a clinician workstation 30 with at least one workflow module or circuit 30c and at least one display 332 in the control room and an additional monitor 32 in the Scanner room 100. The system 10 can be used to guide or direct the placement or movement of at least one MRI compatible interventional and/or surgical tool 50 that is guided into the body using a module or circuit on or in communication with workstation or computer 30. The circuit or module 30c can define the operational protocol to guide the interventional procedure and may include user selectable steps in a workflow and, in some embodiments, allow a user to select a trajectory for inserting a device into the body using the mouse 132 in the scanner room 100 to move a cursor or select GUI actions on the workstation module/circuit in the control room 200 during a surgical MRI guided procedure.

The system 10 can include an MRI scanner interface 40i may be used to allow communication between the workstation 30 and the scanner electronics 20. The interface 40i and/or circuit 30c may be hardware, software or a combination of same. The interface 40 and/or circuit 30c may reside partially or totally in the scanner 20, partially or totally in the (control room and/or Scanner room) workstation 30, or partially or totally in a discrete device therebetween. The system 10 can be configured to render or generate real time visualizations of the target anatomical space using MRI image data and predefined data of at least one surgical tool to segment the image data and place the tool in the rendered visualization in the correct orientation and position in 3D space, anatomically registered to a patient. The tool 50 (FIG. 10) can be a trajectory guide 50t that holds a targeting cannula and/or other interventional components such as a stepped injection cannula.

Figure 2:
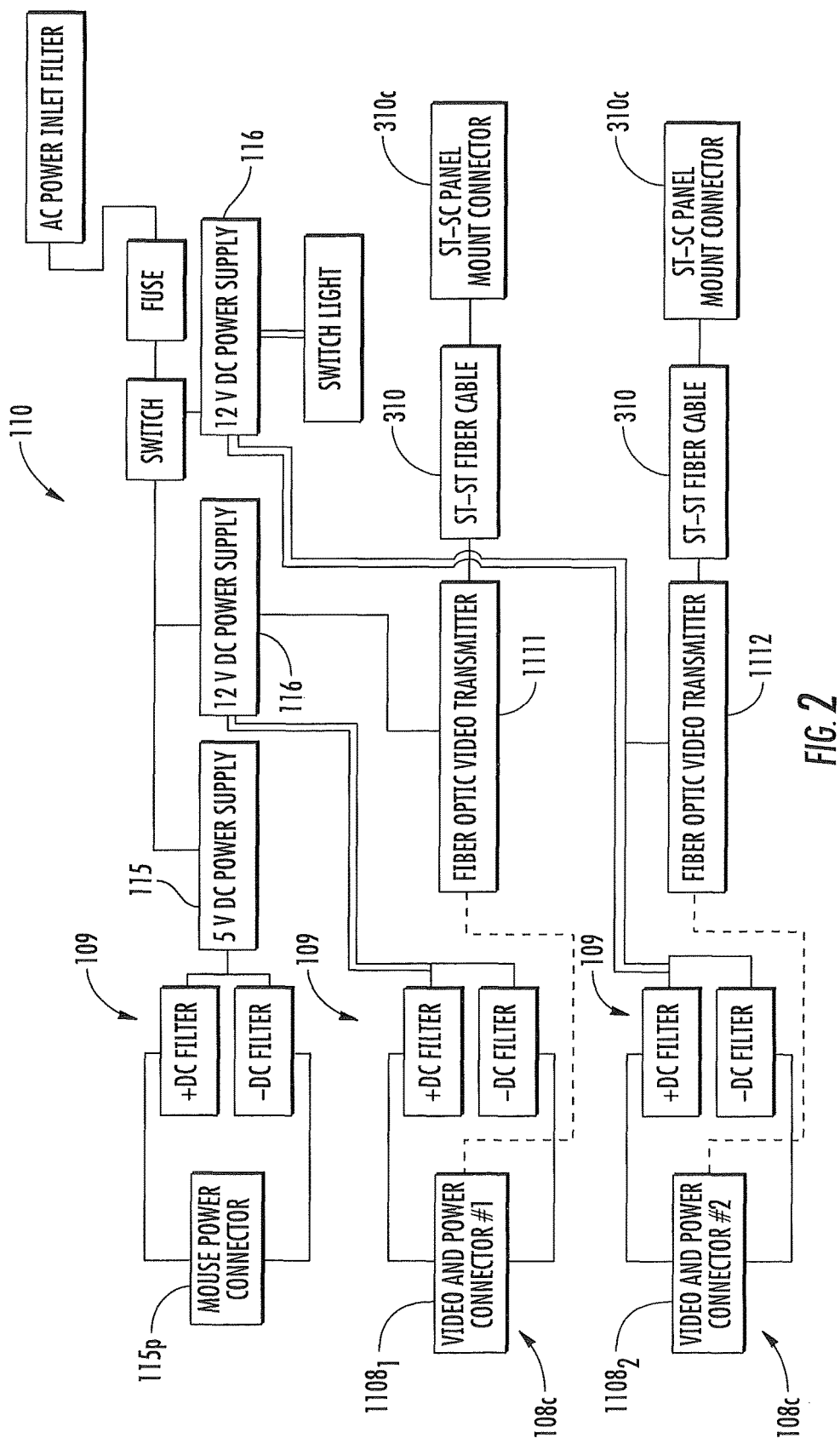
FIG. 2 is a schematic illustration of a dual channel video to fiber optic up-converter and power supply according to embodiments of the present invention.

Referring to FIGS. 1 and 2, the system 10 can also include a (typically dual channel) video to fiber optic signal converter 110 that can be powered via standard 110V AC (in the US). Other power circuits can be used and particularly in countries with different standard AC circuits. This converter 110 can also be configured to hold a DC power supply 115 for the fiber-optic interface 130 for the mouse 132 which is typically a low power source, such as about 5V DC. However, the power supply 115 may be held in a different housing or unit, stand alone, or combined with another operating component.

The mouse 132, mouse interface 130 and converter 110 can be placed in shielded enclosures (e.g., copper ground shields to suppress EMI) and associated power supplies can be filtered.

The dual channel fiber optic to video down converter 110 converts optical signals to composite video that can be sent to existing video processing modules 210i like a screen splitter 210s (FIG. 9).

As shown, the MRI scanner room 100 can include an MRI compatible video monitor 32 which shows the video output of the control room computer workstation 30. This monitor 32 (FIG. 9) connects fiber optically to the monitor output of control room workstation 30 (with computer/laptop). The scanner room mouse 132 controls remote modules, such as software or programs or other modules or circuits 30c, at least partially on or in communication with the control room computer workstation 30.

The system 10 can include a video switch and screen splitter 210 that allows the MRI room monitor display 32 to be selectively switched between the control room computer workstation graphical user interface workflow screen output, which allows the cursor to be moved from the MR Scanner room mouse 132 to select certain features or actions and a video output of the MRI scanner room video camera(s) 108 that can reside in or close to the bore of the magnet to monitor the surgical entry site during an interventional procedure.

The cameras 108, where used, can connect to standard camera cables with connectors 108c, then to the video to fiber optic up-converter 110 to output video signal on fiber optic cable 310 to the control room 200.

Figure 10:
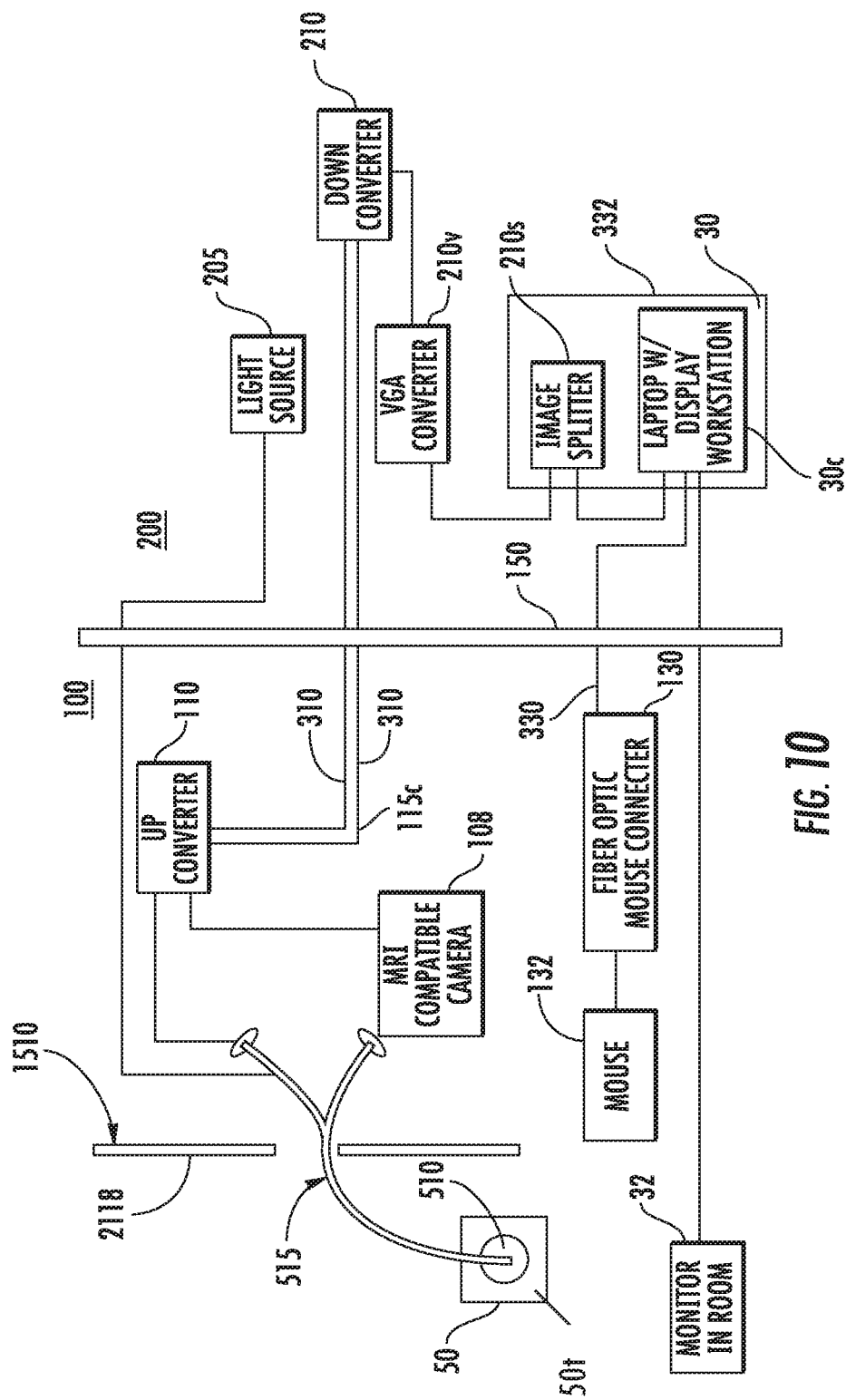
FIG. 10 is another schematic illustration of an MRI suite with fiber optic interfaces for an MRI intervention system according to embodiments of the present invention.

The camera device (fiberscope) 510 (FIG. 9) can have a distal lens and can be configured with a relatively small local field of view (residing proximate the burr hole or surgical entry location) to allow a clinician to monitor the surgical entry point. The fiber-optic camera device 510 can be mounted to a trajectory guide 50t (FIG. 10). The return signal is fed to an MRI compatible video camera 120 and the signal is transmitted as a video of the patient and can be shown in a display or split screen 32 at the workstation 30. One example of a suitable MR compatible video camera is available from MRC Systems GmbH, Heidelberg, Germany.

Figure 3A:
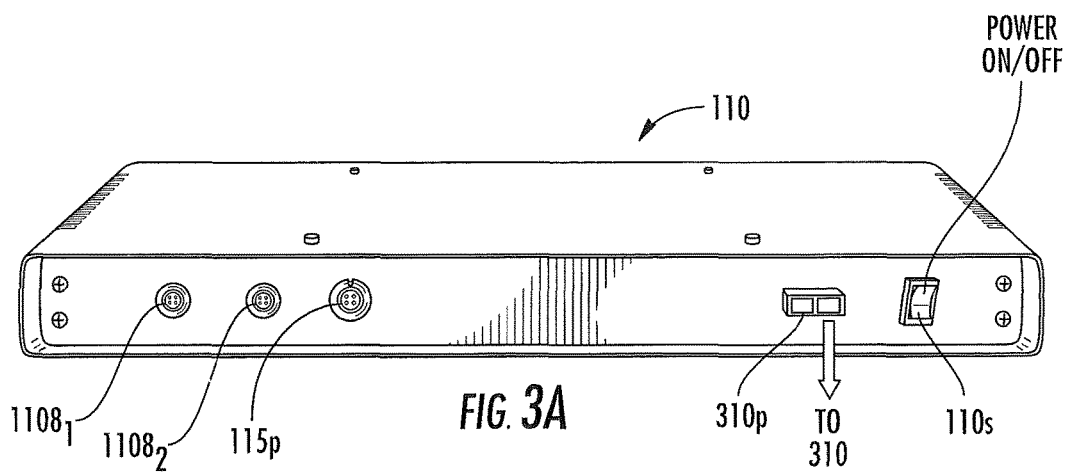
FIG. 3A is a front view of a converter housing (e.g., box) according to embodiments of the present invention.
Figure 3B:
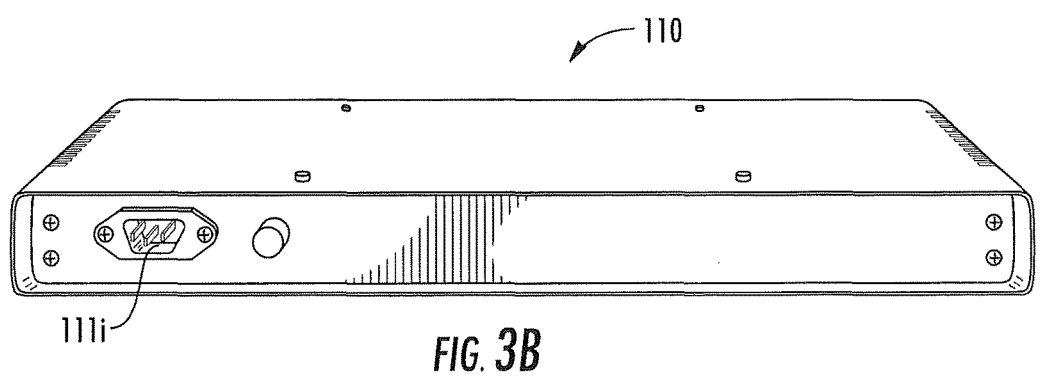
FIG. 3B is a rear view of the converter housing shown in FIG. 3A according to embodiments of the present invention.
Figure 3C:
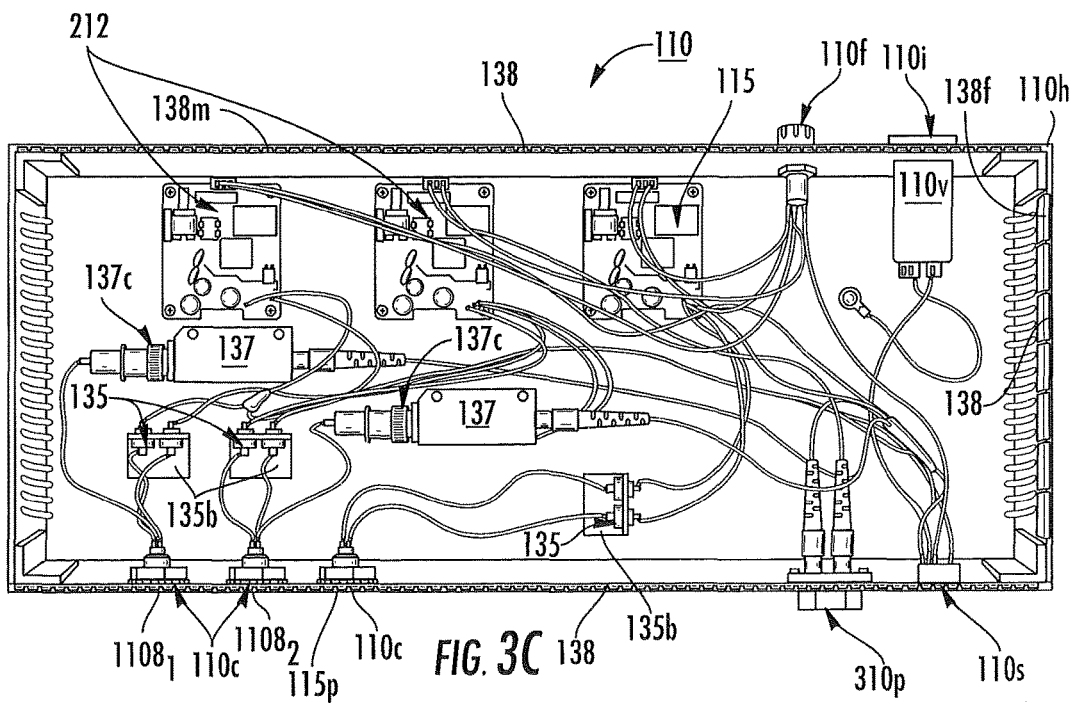
FIG. 3C is a top view of a video to fiber optic up converter and DC power supply with a top cover removed to show an exemplary internal layout of components according to embodiments of the present invention.

FIG. 2 is a schematic illustration of an example of certain components that may be included in the up-converter device 110 which can include at least one video to fiber optic converter, typically two video to fiber optic converters 1111, 1112, These converters can be off-the-shelf devices that are typically used for CCTV application, such as are available from Elcommtech, NY, modified to add EMI grounding shields 138 such as mini-EMI grounding fingers 138m of copper or other suitable material on the long sides and EMI grounding fingers 138f on one or both of the short sides of the perimeter of the housing as shown in FIG. 3C. One suitable converter is the ECT100-MM system which provides a high performance link for transmitting a unidirectional composite video signal over a fiber optic cable 330. Commercially available power supplies such as single 5V DC power supply 115 and two 12 V DC power supplies 116 can be used to supply power to the transmitters 1111, 1112 and to external components—(a) two cameras 108 and (b) mouse fiber optic interface 130. DC filters 109 (positive and negative per video input/connector 108c) can be used to suppress any electromagnetic pulses emitted by the MRI scanner 22 from reaching the power supplies 115, 116 and/or for suppressing any noise from the power supplies from reaching the MRI scanner radio receivers. The transmitters 1111, 1112 can transmit fiber optic video signal to respective fiber optic cables 310 to the control room 200. The cables can be ST-ST fiber cable (single mode duplex fiber optic patch cables) but other fiber optic cables may be used. The cables 310 can include connectors 310c that can be an ST-SC panel connector. However, other connector configurations may be used.

FIGS. 3A and 3B show examples of an up converter box or device 110b that can hold components of the circuit shown in FIG. 2. FIG. 3B shows the rear of the device 110b which includes a power input 111i (e.g., 110 AC). FIG. 3A shows an example of a front of the device 110b that includes connectors 1108$_1$ and 1108$_2$ for respective cameras 108, a mouse power output connector 115p and a fiber optic output port 310p. The inputs and output ports/connectors can be arranged in other manners.

FIG. 3C shows an exemplary camera and mouse power supply that can be incorporated in the video to fiber optic up converter box 110 or may be separate. The device 110 can include 5 VDC and 12 VDC power supplies 115, 212, respectively, from any suitable source including, for example, ICCNexergy, Irvine, Calif. or Cincon Electronics, Ventura, Calif. The device 110 can include at least one (shown as two) fiberoptic transmitter 137, a panel mount dual (or two single) fiberoptic connector 310p to connect dual fiberoptic cable 310, such as 1 m long 62.5, 125 µm with ST connectors from Cable Wholesalers, Livermore, Calif. or Tripp Lite, Chicago, Ill., and other components such as EMI feedthrough filters 135, EMI feedthrough filter brackets 135b, copper contact strips 138m, which may be copper clip-on strips of suitable length (typically 12-20 inches, such as about 16 inches), AC power filter 110v, panel mount, all of which are available from Laird Technologies or Schaffner EMC, Inc. The device 110 can also include a fuse 110f, an externally accessible switch 110s and various connectors 110c mounted to the housing 110h including camera connectors 1108$_1$ and 1108$_2$ (which can be 7 pin female connectors).

Figure 4A:
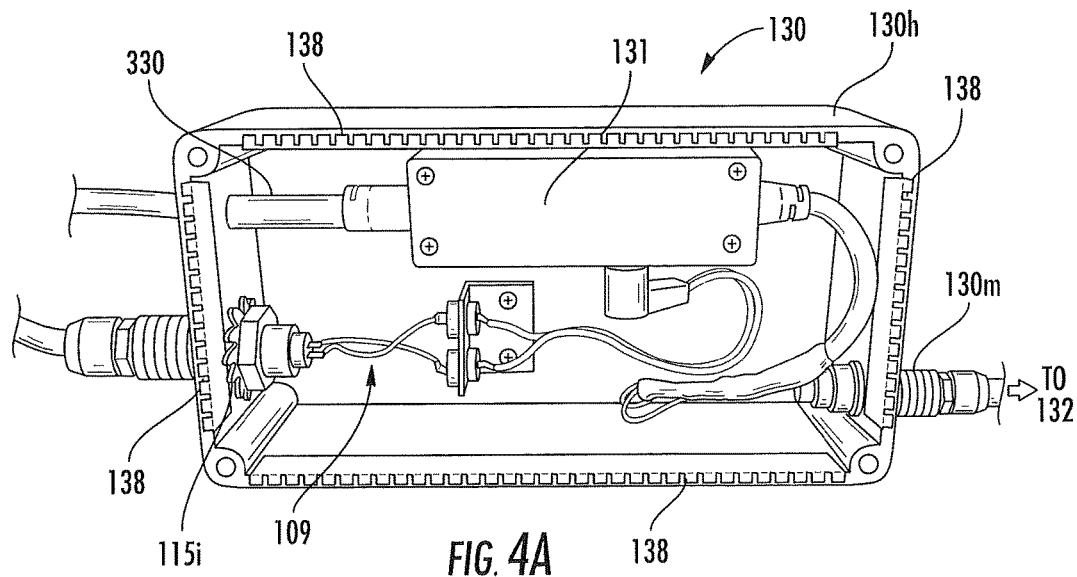
FIG. 4A is a front view of an open fiber optic converter housing with mouse optical interface that can be used proximate an MRI magnet according to embodiments of the present invention.
Figure 4B:
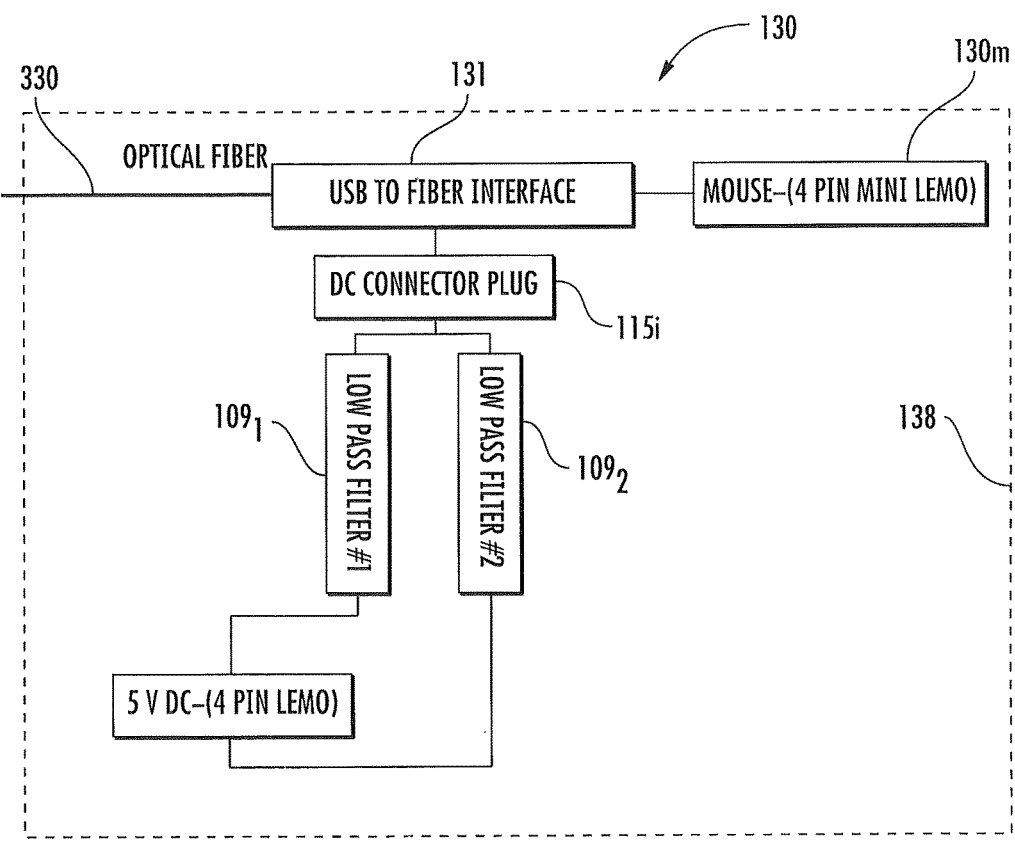
FIG. 4B is a schematic of the USB optical interface shown in FIG. 4A according to embodiments of the present invention.

FIG. 4A shows an example of a mouse fiber optic converter 130. This assembly design can include a modified USB mouse optical interface (e.g., a modified version of an interface available from Opticis Co, South Korea, such as the M2-100) for use near the MRI magnet in the MR scanner room 100. To make the mouse signal converter 130 MRI compatible, the standard 5V DC power supply connector 115i and USB connector 130m can be replaced with non-ferromagnetic components. Also, an RF and/or DC filtering stage 109 can be added to the DC input (FIG. 4B) in order to inhibit or prevent external RF from reaching the optical converter circuitry 131 and potentially causing it to malfunction. The housing 130h can have a perimeter with EMI grounding material 138 such as copper EMI grounding fingers or other suitable configuration.

A relatively long multiple (e.g., four) conductor, fiberoptic or optical cable 330 connects this interface 130 to module 230 outside the scanner room in the control room 200. The fiberoptic cable 330 can be between about 5-50 meters long or longer, typically about 20 meters long. The cable 330 can be obtained from any suitable supplier such as, for example, Lastar Cables 2 Go, Irvine, Calif. and Opticis, Sungnam City, Rep. of Korea. The interface 130 can include an EMI filter and a copper contact strip 138 from any suitable supplier such as Laird or Shaffner EMC referenced above. The control room mouse interface module 230 (FIGS. 1, 5B) can be relatively small and an output cable can connect directly to the USB port 30m of the control room computer/workstation 30. This interface module 230 has the interface electronics that sets up two way communication between the computer 30 and the mouse 132 in the scanner room 100 through the USB port on the computer 30p.

Figure 5A:
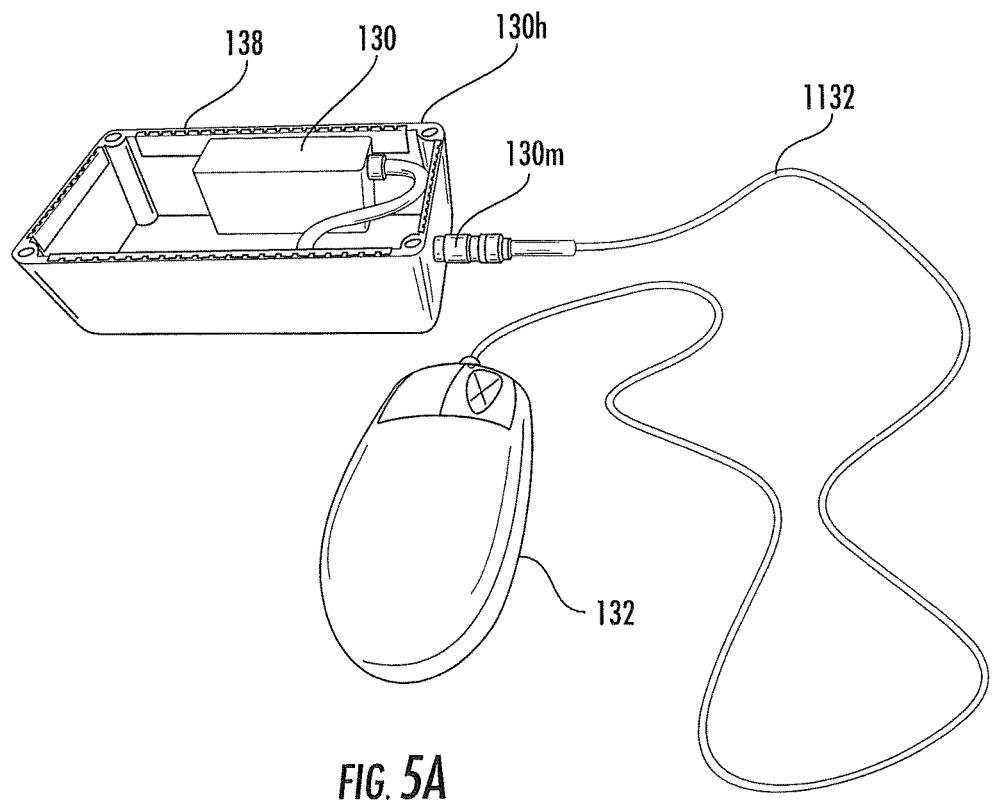
FIG. 5A is a top perspective view of an exemplary MRI-compatible medical grade mouse according to embodiments of the present invention.

As shown in FIG. 5A, the mouse 132 can be a medical grade mouse. The mouse 132 can have a housing 132h that can be easily cleaned and does not typically have a scroll wheel. This is because scroll wheels can be hard to clean to meet medical standards and/or can be quite magnetic and can cause the mouse 132 to be attracted to the magnetic field ($B_0$) of the MRI scanner magnet 22. Thus, in some embodiments, the mouse 132 is an optical mouse which emits a concentrated beam of light that detects the displacement of the mouse itself.

The mouse power cord can be a multi paired 24 AWG shielded cable of suitable length, e.g., between about 1-10 meters, typically about 5 meters.

Figure 5B:
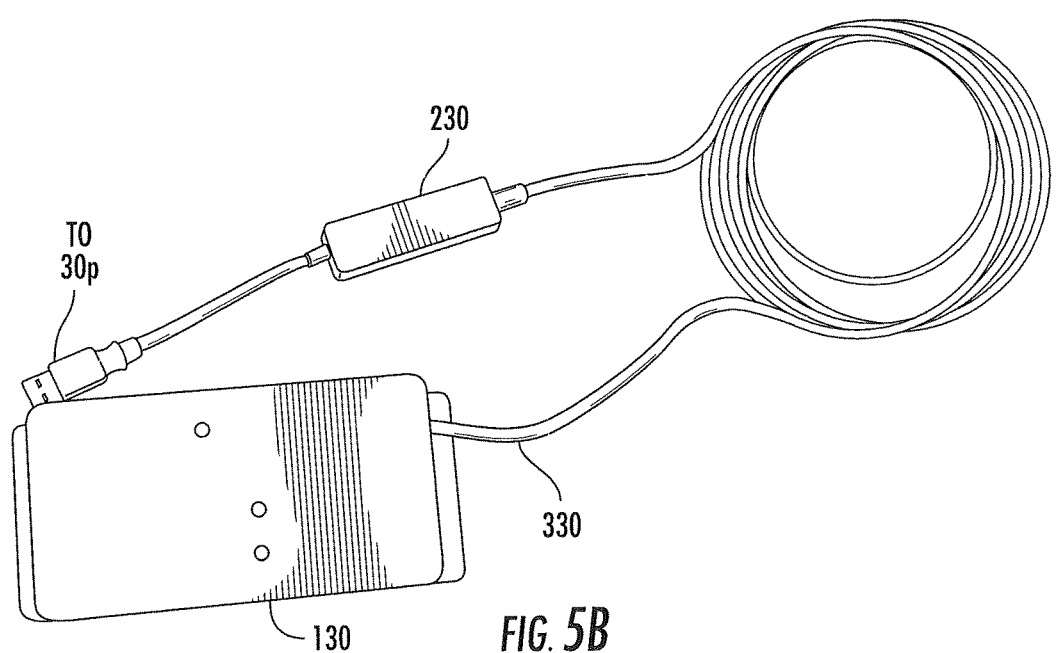
FIG. 5B is a top view of a USB optical interface connected to the control room mouse interface according to embodiments of the present invention.

FIG. 5B illustrates the mouse interface 130 attached to fiber optic cable 330 that can be guided through the waveguide 175 in the RF shielded wall 150 to the control room 200. The fiber optic cable 330 is attached to the mouse/USB interface 230 that allows two way communication between the computer/workstation 30 and the mouse 132 through the USB port 30p of the computer/workstation 30.

In some embodiments, a conventional five button mouse 132 can be modified for use in the MRI scanner room 100 with the fiber optic system 10. Suitable commercially available mouses that can be modified include, for example, those from Man & Machine Inc., Landover, Md., Buy PC Supplies LLC, Fair Lawn, N.J., and the like. The USB connector 132c (FIG. 6A) can include or be replaced with a non-ferromagnetic connector which allows it to be used in close proximity of the MRI magnet without being pulled towards the magnet. An RF shielded cable 1132 can be used to improve RF shielding to the protect the communication lines from the mouse to the fiber optic interface and/or to reduce EMI emissions from the mouse 132 as they can cause artifacts in the MRI images. The shielded cable 1132 can be provided in a suitable length, such as between 10-100 inches, typically 40-70 inches, such as about 60 inches. The cable 1132 and the mouse 132 can be sterilized for medical use in the MRI scanner room.

Figure 6A:
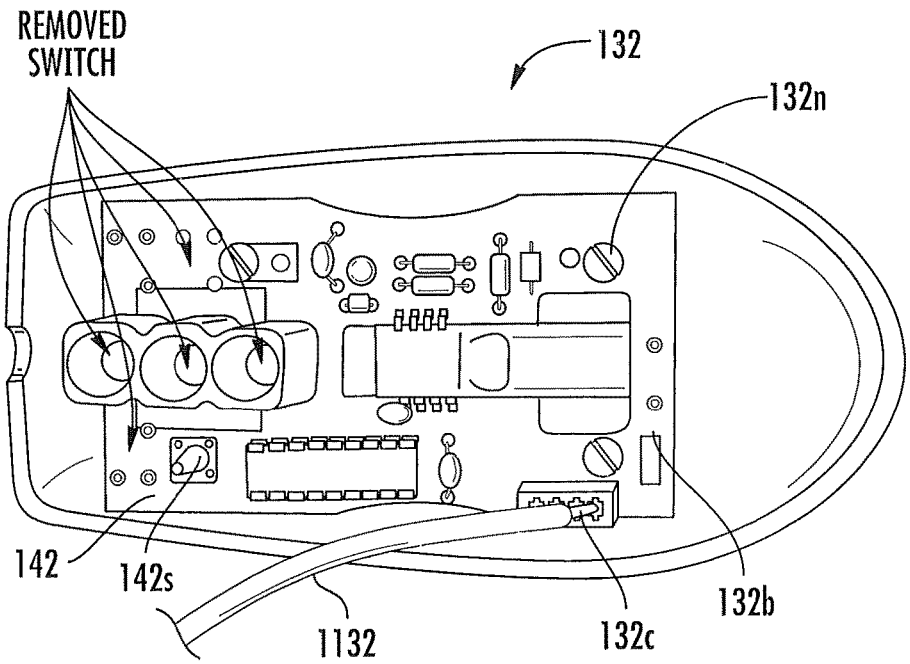
FIG. 6A is a top view of an exemplary mouse with the upper portion of the casing removed to illustrate exemplary internal components according to embodiments of the present invention.

FIG. 6A illustrates that ferromagnetic components like fastener screws that hold an internal circuit board 142 can be replaced with non-magnetic nylon or other suitable non-ferromagnetic screws 132n. As the conventional tactile switches were found to be magnetic, all tactile switches, except one, can be removed. The remaining tactile switch 142s can provide a single input click input, e.g., a "left click" function. As a result of removing the ferromagnetic components, the mouse 132 exhibits very minimal attraction towards the MRI magnet 22.

Figure 6B:
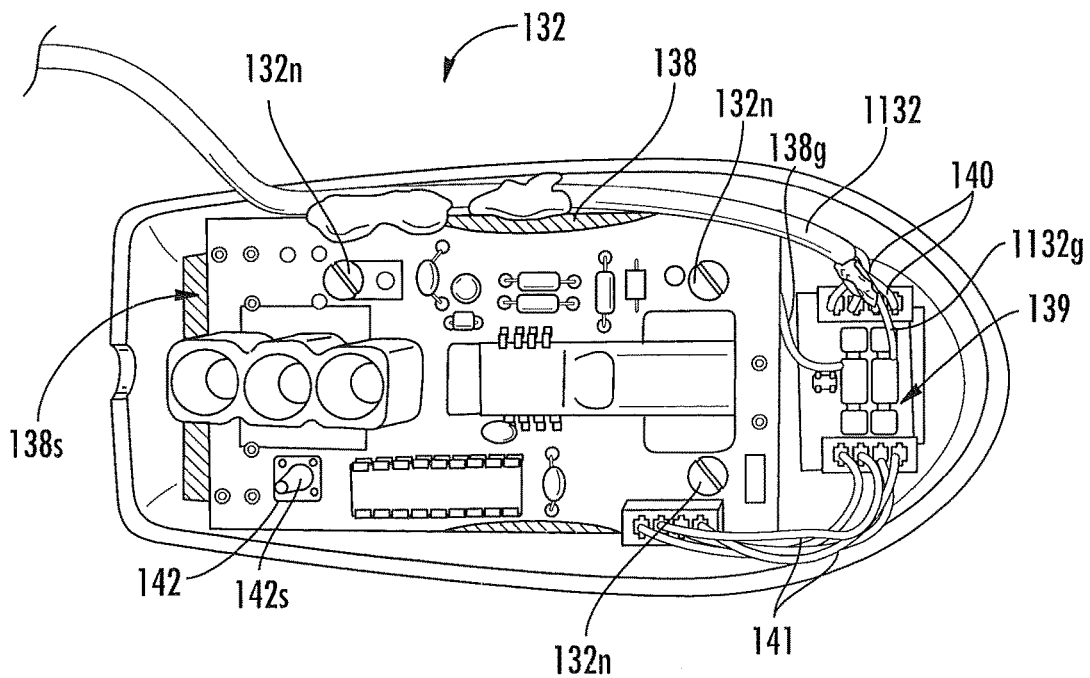
FIG. 6B is a top view of an exemplary mouse with the upper portion of the housing removed to illustrate exemplary internal components according to embodiments of the present invention.

FIG. 6B illustrates that a small "mini" internal circuit board 139 can be used with conventional internal mouse circuit board 142 and/or added to filter the power supply lines/wires 140 and provide serial data lines 141 that connect to the main circuit board 142. The cable connector 132c shown on the main circuit board 142 in FIG. 6A can be on the mini-circuit board 139. Examples of miniature circuit board suppliers include, for example, Pad2Pad, Mahwah, N.J. and Custom Design Services, Oshkosh, Wis. A ground shield 138, which may be a substantially planar sheet of copper or other material 138s, can be provided under the circuit board 132b to suppress EMI. As shown in FIG. 6C, the ground shield 138 can be substantially coextensive with the body of the circuit board 132b and typically covers at least a major portion of a length and width thereof. The ground shield 138 can comprise foil, such as copper foil, for example. The mini circuit board 139 can provide electrical connection to the two grounds 1132g, 138g and respective EMI suppressors 237 and/or to provide the EMI filter 233.

Figure 6D:
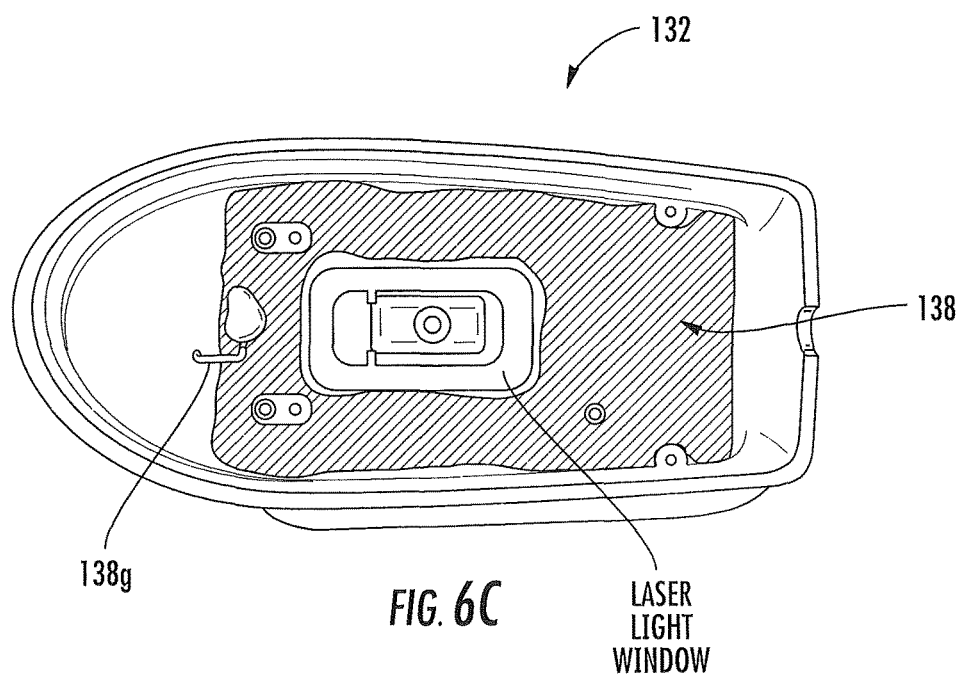
FIG. 6D is a top view of the mini circuit board without cabling and adjacent exemplary spacers according to embodiments of the present invention.
Figure 6D:
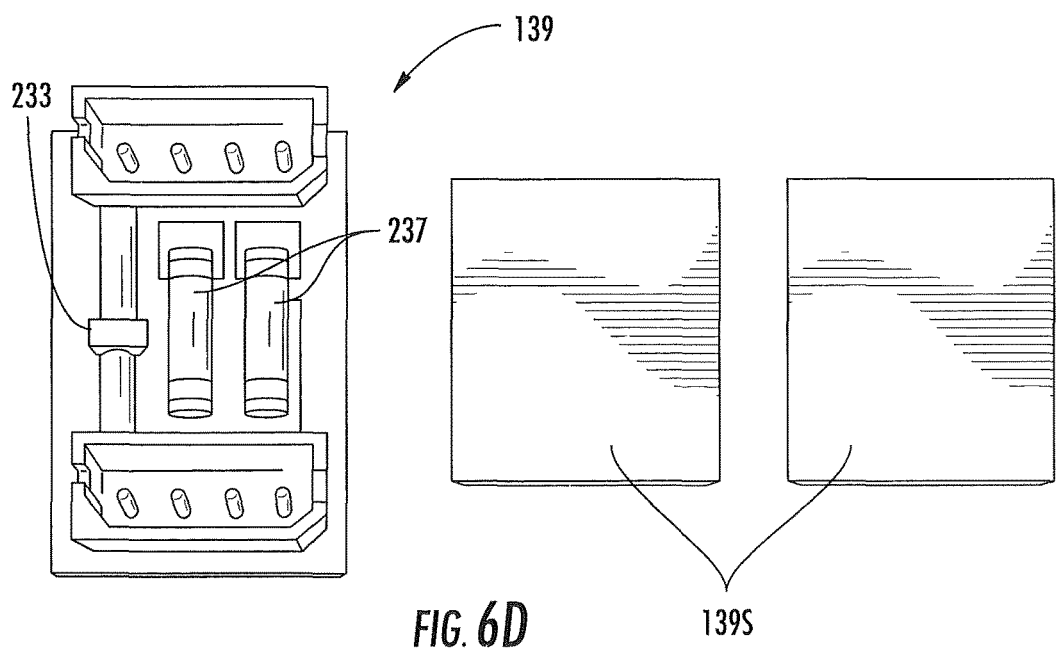

As shown in FIG. 6D, the mini-circuit board 139 can include first and second EMI suppressors 237. The suppressors are available from suitable sources including, for example, Laird Technologies, Earth City, Mo. and Schaffner EMC, Inc., Edison, N.J. The mouse 132 can also include one or more EMI filters 233 such as those available from Laird Technologies, Earth City, Mo. and Schaffner EMC Inc, Edison, N.J. The circuit board 139 can be held on one or more stacked fiberglass spacers 139s. The grounding wire 138g connected to the shield 138 can be routed up and attached to a center on the first EMI suppressor 237. No connection is needed from the mouse PCB 142 to the shield (e.g., copper foil) 138. A grounding wire 1132g from a shield of the mouse cable 1132 can be connected to the other suppressor 237 (shown as the front suppressor).

While the above description provides that a conventionally or commercially available mouse 132 can be modified for the uses noted herein, a custom mouse 132 can be provided which has the desired non-ferromagnetic components, at least one EMI filter(s), EMI suppressor(s), RF shielding, user input and/or other components and configurations.

Figure 7:
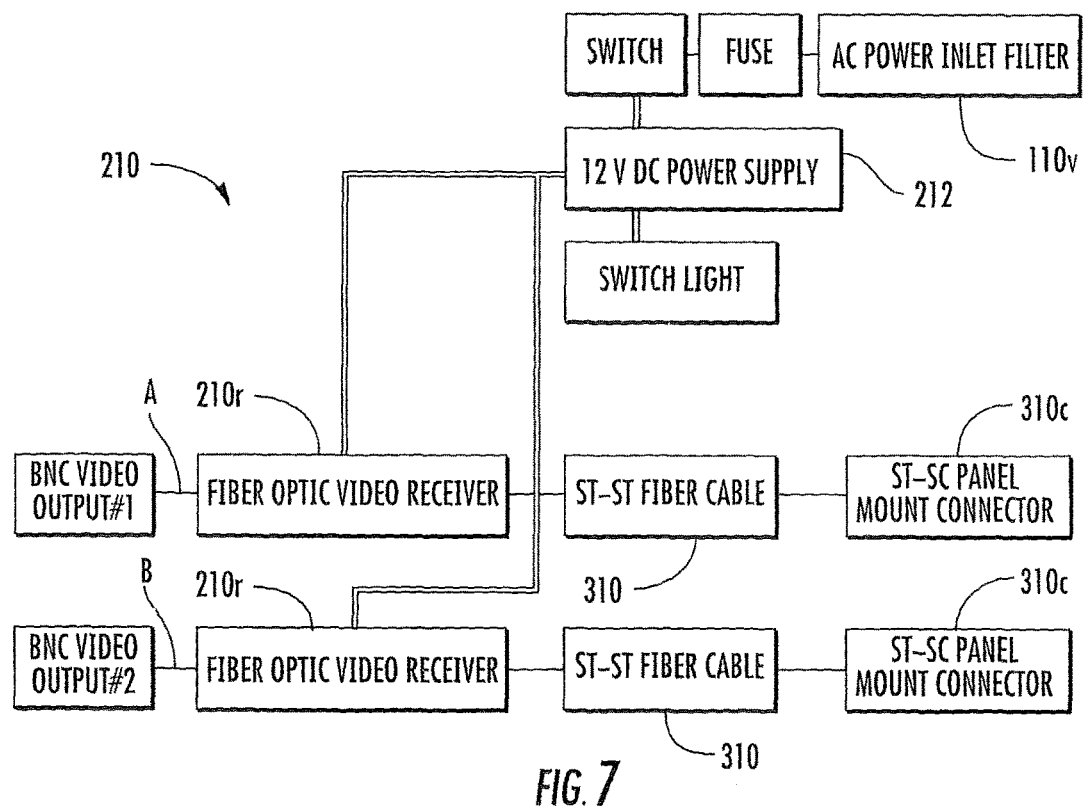
FIG. 7 is a schematic illustration of an exemplary fiber optic to video down-converter circuit according to embodiments of the present invention.

FIG. 7 shows an example of an interface with the fiber optic to video down-converter 210 according to some embodiments of the present invention. As shown, this device 210 has fiber optic receivers 210r that convert optic signals from inside the MRI suite (control room 200) to composite video (BNC) signals A, B which can easily be handled by the existing screen splitter 210s and video selector switch assemblies. The converter 210 can include a built-in 12V DC power supply 212 for powering the optical receiver electronics. FIG. 7 shows an exemplary system layout of the box. The 12 VDC power supply can be obtained from any suitable supplier including, for example, ICCNexergy, Irvine, Calif. and Cincon Electronics, Ventura, Calif. The fiberoptic receivers 210r can be obtained from Telecast Fiber Systems, Worcester, Mass. or Kramer Electronics, Hampton, N.J. or other suitable suppliers. The copper ground material 138 can be obtained from Laird or Schaffer and the dual fiberoptic cable can be provided in suitable lengths, typically between 0.5 m to about 5 meters, more typically about 1 meter and can be obtained from Cable Wholesalers or Tripp Lite as referenced above.

Figure 8A:
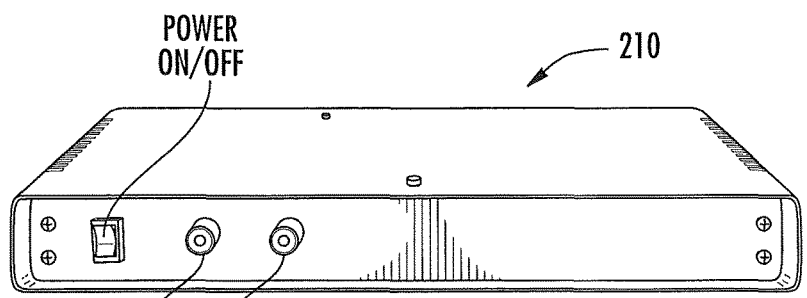
FIG. 8A is a front view of a housing holding the converter circuit of FIG. 7 suitable for use in the control room according to embodiments of the present invention.
Figure 8B:
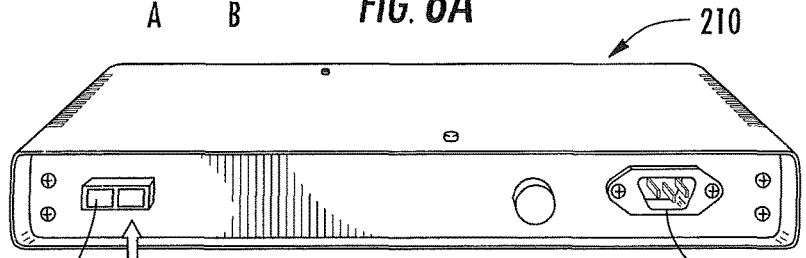
FIG. 8B is a rear view of the converter housing shown in FIG. 8A.

FIGS. 8A and 8B show examples of a front and back view of this interface device 210. The back can include the AC power input 210p and optical input connector 1310c that connects fiber optic cable 310 from the scanner room 100. FIG. 8A shows the BNC video output A, B that can connect to monitor 332 of the workstation 30.

Figure 8C:
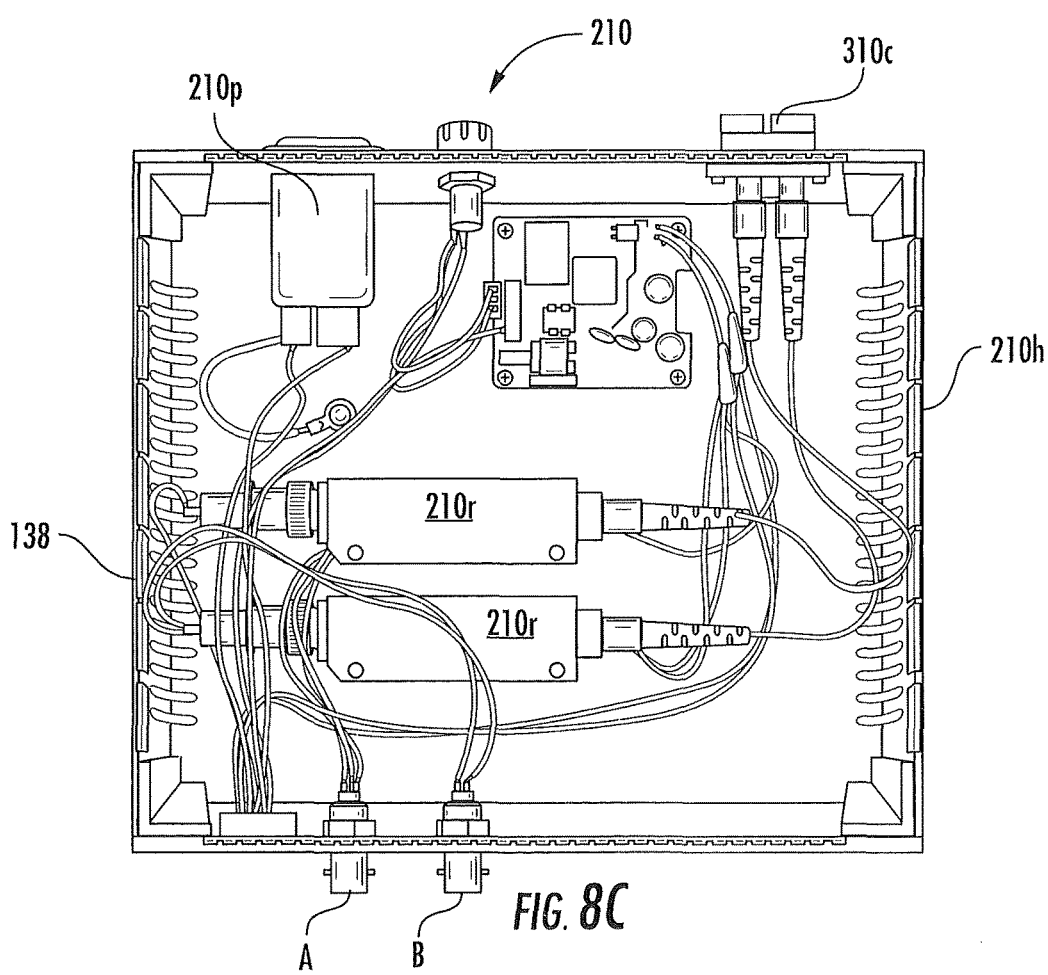
FIG. 8C is a top view of the control room converter illustrating exemplary components according to embodiments of the present invention.

FIG. 8C illustrates an exemplary housing 210h with a perimeter (at least three sides) having EMI grounding material such as EMI fingers 138f or mini fingers 138m, such as copper or other suitable EMI shielding material.

FIG. 9 is an electrical layout of certain components of the system 10 according to embodiments of the present invention. As shown, in the scanner room 100, the monitor 32 (which can be a 32 inch IEC 60601-1 compliant monitor) can be powered by power supply 32p (which can be a 12V DC power supply which can also be 60601-1 compliant). As is known to those of skill in the art, IEC 60601 is a series of technical standards for the safety and effectiveness of medical electrical equipment, published by the International Electrotechnical Commission. The monitor 32 is MR compatible and can be obtained from Resonance Technology, Inc., Northridge, Calif. or NordicNeuroLab, Milwaukee, Wis.

The system 10 can include fiberscopes 515 and an associated light source 205. The light source can be obtained from Precision Optics Corporation, Gardner, Mass. or Specialty Optical, Los Alamos, N. Mex.

The up converter and power supply 110 can communicate with the mouse interface 130 and monitor power supply 32p as well as the cameras 108. Fiberoptic cables 310, 330 connect to components in the control room 290 through the RF shielded wall 150, through a patch or penetration panel and/or waveguide 175. The signal 32f from the fiberoptic mouse cable input 310 can connect to the USB port of the workstation/computer 30 outside the Scanner room such as in the control room 200, so that a user in the scanner room 100 can direct cursor movement on the monitor 332 to direct MRI guided interventions controlled by a module on or in communication with the workstation 30 and/or monitor 332. The shaded components in the control room 200 can receive power from isolation transformers. The screen splitter 210s can be powered by a low voltage screen splitter power supply (e.g., 5 V DC) and the BNC to VGA converter 210v can be powered by a 12 VDC power supply 1210p, the VGA switch box 210sw can be powered by a 6 VDC power supply 1210sw. However, it is contemplated that other power supplies, power supply ranges and power supply configurations may be used FIG. 10 illustrates the system 10 with cameras 108, sterile drape 2118, fiber bundle 115 for the fiberscopes 510 that cooperate with a surgical to 50 that includes a trajectory guide 50 t which can be controlled by mouse 132 via fiber optic cable to indicate a cursor movement on monitor 332 or workstation 30 in the control room 200. The system 10 can be used with a neurological surgical intervention system. The trajectory guide 50 can define deep brain access of interventional devices. The visualizations on the monitor or display 32 in the control room 200 can include split screens which can allow both camera views and rendered visualizations that can combine multiple sources of data to provide visualizations of spatially encoded tool position and orientation with anatomical structure. The mouse 132 in the MR Scanner room 100 can be in communication with the circuit in the MR control room 200 that has an interactive operational workflow program.

Figure 11A:
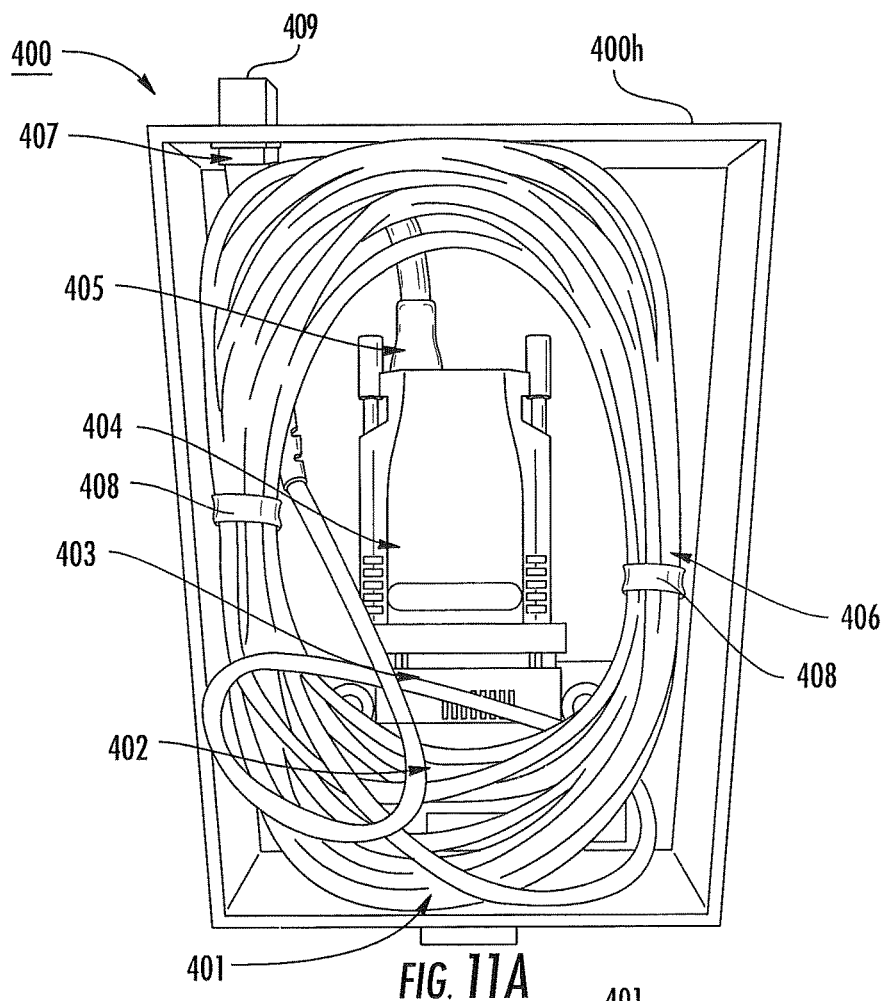
FIG. 11A is a top view of an exemplary transmitter interface assembly (with the top cover removed) according to embodiments of the present invention.
Figure 11B:
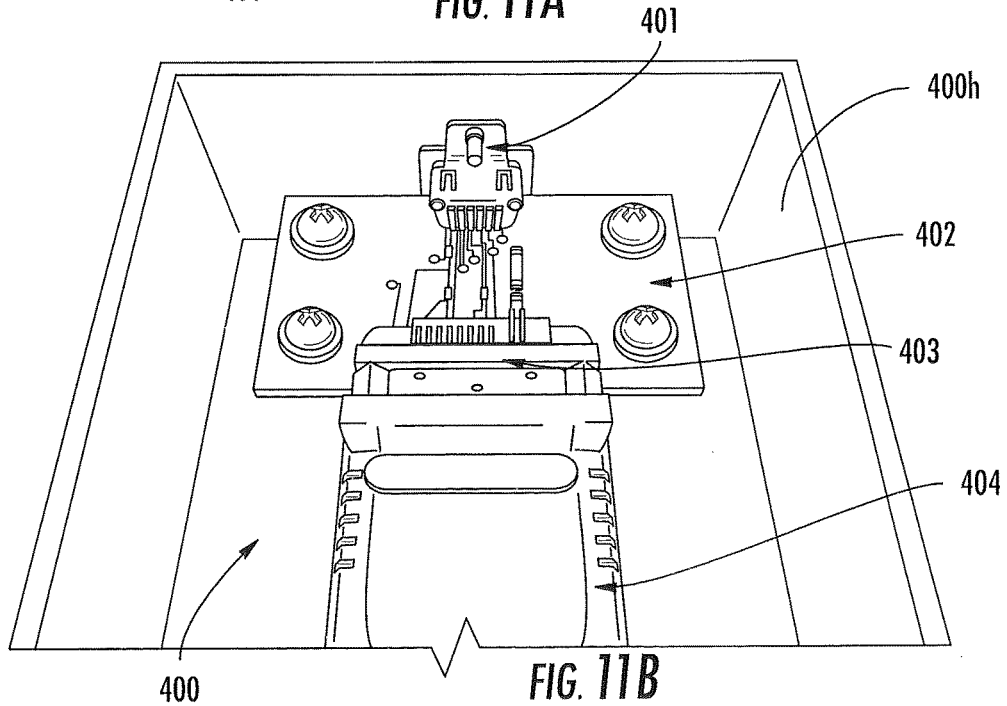
FIG. 11B is an enlarged partial top view of the device shown in FIG. 11A (with cabling omitted for ease of reference) according to embodiments of the present invention.

FIGS. 11A and 11B illustrate examples of the transmitter interface assembly 400. As shown, the assembly 400 includes a housing 400h that holds an HDMI (High Definition Multimedia Interface) connector 401, an HDMI to DVI (Digital Video Interface) circuit board 402, a DVI connector 403, the transmitter 404 (also called the fiberoptic converter as it converts video to fiber optic signal), fiberoptic output 405, fiberoptic cable 406, and fiberoptic output to monitor power supply 407 (which can include "dust cover 409" when not in use). Where long lengths of cable 406 are used inside the housing 400h, tie wraps 408 or other components may hold the bundles together. The transmitter 404 can be any suitable transmitter such as is available from Schaffner EMC, Inc., Edison, N.J. The housing 400h is configured to shield the transmitter 404 from RF and other undesired operational signal.

The circuit board 402 allows connection of the two different connectors 401, 403 while keeping sufficient separation between the many (e.g., about 19 or so) different electrical paths. The tight fitting housing 404h provides a suitable RF shield. It is made of suitable shielding material, such as, for example, aluminum with a chemical film coating. The enclosure 404h can have shielding capabilities of up to 60 dB at 3 GHz. Other shielding may have less or more capability and still perform appropriately, typically with at least 20 dB in the frequencies of operation. One example of a commercially available shield is available from Compac as an RFT Series Enclosures have shielding capabilities to 60 dB at 3 GHz. The transmitter 404 can be obtained from NordicNeuroLab, Milwaukee, Wis., under part number 101041, the manufacturer of the monitor 32. The transmitter 404 communicates with the receiver 32r (FIG. 1) that is mounted inside the monitor 32.

In particular embodiments, the systems define and present workflow with discrete steps for finding target and entry point(s), localizing the entry point(s) to a physical identified grid position, guiding the alignment of the targeting canula to a planned trajectory, monitoring the insertion of the probe, and adjusting the X-Y position in cases where the placement needs to be corrected. During steps where specific MR scans are used, the circuit or computer module can display data for scan plane center and angulation to be entered at the console. The workstation/circuit 30 can passively or actively communicate with the MR scanner control cabinet 20. The system can also be configured to use functional patient data (e.g., fiber tracks, fMRI and the like) to help plan or refine a target surgical site.

Embodiments of the present invention can be configured to carry out diagnostic and interventional procedures such as to guide and/or place interventional devices to any desired internal region of the body or object, but may be particularly suitable for neurosurgeries. The object can be any object, and may be particularly suitable for animal and/or human subjects. The MRI intervention system can include a trajectory guide for delivery of a therapeutic drug or substance and/or a stimulation lead to a desired location in the body, such as in the brain. The system can be used for gene and/or stem-cell based therapy delivery or other neural therapy delivery and allow user-defined custom targets in the brain or to other locations. In addition, embodiments of the systems can be used to ablate tissue in the brain or other locations. In some embodiments, it is contemplated that the systems can be configured to treat AFIB in cardiac tissue, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

Examples of known treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

Figure 12:
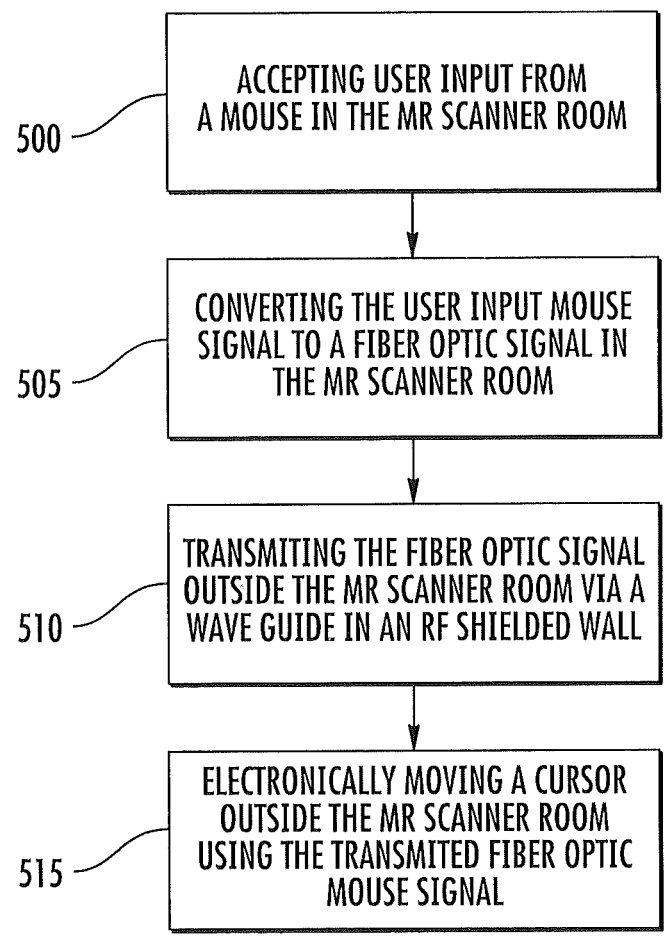
FIG. 12 is a flow chart of exemplary operations that can carry out embodiments of the present invention.

FIG. 12 illustrates exemplary operations that can be used to carry out embodiments of the present invention for controlling an MRI guided surgery, interventional procedure or diagnostic procedure. User input from a mouse in an MR scanner room of an MRI suite is accepted (block 500). Signal from the mouse is converted to a fiber optic mouse signal in the MR scanner room (block 505). The fiber optic mouse signal is transmitted to a USB port on a computer outside the MR scanner room via a fiberoptic cable that is routed through a waveguide in an RF shielded wall between the MR scanner room and an MR control room of the MRI suite (block 510). A cursor on a monitor outside the MR scanner room in communication with the computer is electronically moved using the transmitted fiber optic mouse signal (block 515).

The moving can be carried out to control actions in a defined workflow associated with an MRI guided surgical procedure provided by the computer outside the scanner room to the outside the scanner room.

The method can include transmitting fiber optic signal from the computer in the control room to a monitor in the MR Scanner room while the mouse is detached and/or not attached to the monitor in the MR Scanner room.

Embodiments of the present invention may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks, The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

The MRI scanner 20 can include a console that has a "launch" application or portal for allowing communication to the circuit 30c of the workstation 30. The scanner console can acquire volumetric T1-weighted (post-contrast scan) data or other image data (e.g., high resolution image data for a specific volume) of a patient's head or other anatomy. In some embodiments, the console can push DICOM images or other suitable image data to the workstation 30 and/or circuit 30c. The workstation 30 and/or circuit 30c can be configured to passively wait for data to be sent from the MR scanner 20 and the circuit 30c/workstation 30 does not query the Scanner or initiate a communication to the Scanner. In other embodiments, a dynamic or active communication protocol between the circuit 30c/workstation 30 and the Scanner 20 may be used to acquire image data and initiate or request particular scans and/or scan volumes. Also, in some embodiments, pre-DICOM, but reconstructed image data, can be sent to the circuit 30c/workstation 30 for processing or display. In other embodiments, pre-reconstruction image data (e.g., substantially "raw" image data) can be sent to the circuit 30c/workstation 30 for Fourier Transform and reconstruction.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical system for an MRI suite, comprising:
   an MRI compatible mouse residing in an MR Scanner room of the MRI suite, wherein the mouse is an optical mouse which emits a beam of light for detecting displacement of the mouse based on user movement of the mouse to thereby operate without a scroll wheel, wherein the mouse has a primary circuit board in a mouse housing, and wherein the mouse further comprises first and second EMI suppressors, one with a ground input connected to an EMI ground shield and one with a ground input connected to a shield of an RF shielded cable;
   a fiber optic mouse interface in the MR Scanner room in communication with the mouse;
   a length of the RF shielded cable attached to the mouse and extending between the mouse and the fiber optic mouse interface in the MR Scanner room, wherein the RF shielded cable provides a power input to the mouse and transmits and receives electrical signal in response to movement of the mouse; and
   a fiber optic cable attached to the fiber optic mouse interface configured to connect a computer outside the MR Scanner room so that a user is able to move the mouse in the MR Scanner room to (i) move a cursor and (ii) select functions or actions in drop down menus presented by the computer to at least one monitor.

2. The system of claim 1, wherein the fiber optic cable is a first fiber optic cable, the system further comprising an up-converter device in the MR scanner room in communication with a down-converter device outside the MR Scanner room, wherein video from at least one camera in the MR Scanner room is converted to fiber optic signal and transmitted by the up-converter to the down-converter by a second fiber optic cable separate from the first fiber optic cable which converts the fiber optic signal back to video and transmits the video to a monitor outside the MR Scanner room, and wherein the up-converter device provides a power supply to the fiber optic mouse interface that powers the mouse and a power supply to the at least one camera.

3. The system of claim 2, wherein the up-converter device comprises a DC power supply that is configured to power the fiber optic mouse interface and the fiber optic mouse interface has a power outlet that attaches to the RF shielded cable that powers the mouse.

4. The system of claim 3, wherein the up-converter device comprises a housing having a perimeter with at least a portion having a ground shield to suppress EMI.

5. The system of claim 1, wherein the fiber optic cable is routed through a waveguide in an RF shielded wall that extends between the MR Scanner room and an MR control room of the MRI suite.

6. The system of claim 1, wherein the fiber optic mouse interface comprises a USB to optical converter and non-ferromagnetic housing with EMI grounding, power input and one or more USB mouse connectors, and wherein the fiber optic mouse interface is connected to the RF shielded cable.

7. The system of claim 6, wherein the fiber optic mouse interface comprises a housing with a perimeter having a ground shield on walls thereof.

8. The system of claim 1, wherein the mouse has a single operational external tactile switch allowing for left click input.

9. The system of claim 1, wherein the mouse has non-ferromagnetic screws holding the primary circuit board in the mouse housing.

10. The system of Claim 1, wherein the mouse further comprises a second circuit board holding the first and second EMI suppressors, DC power supply filter wires and serial data lines that connect to the primary circuit board.

11. The system of claim 1, further comprising a video to fiber optic up-converter device in the MR scanner room, the up-converter device comprising at least one camera connector port, a mouse power port, a fiber optic output port and an AC voltage power input port, wherein the mouse power port is configured to engage a power cord that supplies DC voltage to the fiber optic mouse interface.

12. The system of claim 1, further comprising a fiber optic to video down-converter device outside the MR scanner room, the down-converter device in communication with the computer and at least one monitor, the down-converter device comprising at least one optical input port configured to engage a fiber optic cable, at least one fiber optic video receiver, and at least one BNC video output.

13. The system of claim 1, further comprising a monitor in the MR Scanner room that is connected to a VGA switch outside the MR Scanner room via a fiberoptic monitor cable, and wherein the mouse is not attached to the monitor in the MR Scanner room.

14. A method of controlling an MRI guided surgery, comprising;
   accepting user input from a mouse in an MR Scanner room of an MRI suite, wherein the mouse comprises first and second EMI suppressors, one with a ground input connected to an EMI ground shield and one with a ground input connected to a shield of an RF shielded cable;
   obtaining electrical signal associated with the user input using the RF shielded cable in the MR Scanner room that is attached to the mouse and that also powers the mouse;
   converting signal from the mouse to a fiber optic mouse signal in the MR Scanner room;
   transmitting the fiber optic mouse signal to a USB port on a computer outside the MR Scanner room via a first fiberoptic cable that is routed through a waveguide in an RF shielded wall between the MR Scanner room and an MR control room of the MRI suite;
   electronically moving a cursor and/or selecting actions or functions on a monitor with the computer using the transmitted fiber optic mouse signal;
   obtaining video signal from at least one camera in the MR Scanner room;

up-converting the obtained video signal to a fiber optic signal in the MR Scanner room;

transmitting the converted video signal via a second fiberoptic cable that is routed through the waveguide in the RF shielded wall;

down-converting the video signal from the second fiberoptic cable outside the MR Scanner room; and displaying the down-converted signal on a display.

15. The method of claim 14, wherein the monitor is outside the MR Scanner room, and wherein the moving step is carried out to control actions in a defined programmatically controlled workflow associated with an MRI guided surgical procedure provided by the computer outside the MR Scanner room.

16. The method of claim 14, further comprising transmitting fiber optic signal from the computer outside the MR Scanner room to a monitor in the MR Scanner room, wherein the mouse is not attached to the monitor in the MR Scanner room.

17. A surgical system for an MRI suite, comprising:

an MRI compatible mouse residing in an MR Scanner room of the MRI suite, wherein the mouse comprises first and second EMI suppressors, one with a ground input connected to an EMI ground shield and one with a ground input connected to a shield of an RF shielded cable;

a fiber optic mouse interface in the MR Scanner room in communication with the mouse;

a first fiber optic cable attached to the fiber optic mouse interface connected to a computer in communication with at least one monitor outside the MR Scanner room so that a user is able to move the mouse in the MR Scanner room to (i) move a cursor and/or (ii) select functions or actions in drop down menus presented by the monitor outside the MR Scanner room;

at least one camera attached to a camera cable in the MR Scanner room; and an up-converter device in the MR Scanner room attached to the camera cable and a second fiber optic cable spaced apart from the first fiber optic cable in the MR Scanner room and in communication with a down-converter device outside the MR Scanner room, wherein video to fiber optic signal from the second fiber optic cable is converted and transmitted by the up-converter to the down-converter which converts fiber optic signal to video.

18. The system of claim 17, further comprising a monitor in the MR Scanner room that is connected to a VGA switch outside the MR Scanner room via a fiberoptic monitor cable, and wherein the mouse is not attached to the monitor in the MR Scanner room.

19. The system of claim 17, further comprising a transmitter interface assembly residing in the MR control room in communication with the down converter in the MR control room and a monitor in the MR Scanner room.

20. A MRI compatible fiber optic mouse suitable for operation in a an MRI Scanner room of a medical MRI suite holding a high field magnet, comprising:

an MRI compatible mouse housing comprising non-ferromagnetic screws holding a primary circuit board therein, wherein the primary circuit board is connected to an RF shielded cable extending externally from the mouse housing;

a single operational external tactile switch allowing for left click input held by the mouse housing;

an EMI ground shield residing in the mouse housing under the primary circuit board; and first and second EMI suppressors and at least one EMI filter in electrical communication with the primary circuit board.

21. The mouse of claim 20, further comprising a second circuit board in the mouse housing, adjacent the primary circuit board, and having a smaller area than the primary circuit board, wherein the second circuit board holds DC power supply filter wires that are in electrical communication with the RF shielded cable and also holds serial data lines that connect to the primary circuit board.

22. A MRI compatible fiber optic mouse suitable for operation in a an MRI Scanner room of a medical MRI suite holding a high field magnet, comprising:

an MRI compatible mouse housing comprising non-ferromagnetic screws holding a primary circuit board therein;

a single operational external tactile switch allowing for left click input held by the mouse housing; and an EMI ground shield residing in the mouse housing under the primary circuit board, wherein the mouse is sterile for use in a surgical environment, and wherein the mouse further comprises first and second EMI suppressors, one with a ground input connected to the EMI ground shield and one with a ground input connected to a shield of a cable attached to the mouse and extending external thereof.

* * * * *

UNITED STATES PATENT AND TRADEMARK OFFICE
CERTIFICATE OF CORRECTION

PATENT NO. : 9,610,048 B2
APPLICATION NO. : 13/772822
DATED : April 4, 2017
INVENTOR(S) : Vij et al.

Page 1 of 1

It is certified that error appears in the above-identified patent and that said Letters Patent is hereby corrected as shown below:

In the Specification

Column 13, Line 62: Please correct "surgical to 50" to read -- surgical tool 50 --

In the Claims

Column 20, Claim 20, Line 9: Please correct "operation in a an MRI" to read -- operation in an MRI --

Claim 22, Line 31: Please correct "operation in a an MRI" to read -- operation in an MRI --

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*